United States Patent
Mori et al.

(10) Patent No.: US 8,945,919 B2
(45) Date of Patent: Feb. 3, 2015

(54) METHODS AND COMPOSITION FOR TREATING NEURAL DEGENERATION

(75) Inventors: Keita Mori, Cupertino, CA (US); Martha C. Bohn, Gary, IN (US); Ciara Tate, San Francisco, CA (US); Irina Aizman, Mountain View, CA (US); Aleksandra Glavaski, Chicago, IL (US); Tamas Virag, Kensington, MD (US)

(73) Assignee: San Bio, Inc., Mountain View, CA (US)

( * ) Notice: Subject to any disclaimer, the term of this patent is extended or adjusted under 35 U.S.C. 154(b) by 820 days.

(21) Appl. No.: 12/733,108

(22) PCT Filed: Aug. 14, 2008

(86) PCT No.: PCT/US2008/009731
§ 371 (c)(1),
(2), (4) Date: Jun. 10, 2010

(87) PCT Pub. No.: WO2009/023251
PCT Pub. Date: Feb. 19, 2009

(65) Prior Publication Data
US 2010/0266554 A1 Oct. 21, 2010

Related U.S. Application Data

(60) Provisional application No. 60/964,763, filed on Aug. 15, 2007, provisional application No. 61/000,972, filed on Oct. 30, 2007, provisional application No. 61/005,181, filed on Dec. 3, 2007, provisional application No. 61/125,991, filed on Apr. 30, 2008.

(51) Int. Cl.
*A61K 35/12* (2006.01)
*A61P 25/00* (2006.01)
*C12N 15/87* (2006.01)
*A61K 35/28* (2006.01)
*C12N 5/079* (2010.01)
*C12N 5/0775* (2010.01)

(52) U.S. Cl.
CPC ............ *A61K 35/28* (2013.01); *C12N 5/0618* (2013.01); *C12N 5/0663* (2013.01); *A61K 2035/124* (2013.01); *C12N 2501/42* (2013.01); *C12N 2510/00* (2013.01); *C12N 2502/1394* (2013.01); *C12N 2506/1353* (2013.01)

USPC .......... 435/368; 435/455; 435/325; 424/93.7

(58) Field of Classification Search
None
See application file for complete search history.

(56) References Cited

U.S. PATENT DOCUMENTS

| | | |
|---|---|---|
| 6,989,271 B2 | 1/2006 | Dezawa et al. |
| 2003/0003090 A1 | 1/2003 | Prockop et al. |
| 2006/0166362 A1 | 7/2006 | Dezawa et al. |
| 2006/0216276 A1 | 9/2006 | Dezawa et al. |
| 2006/0233765 A1 * | 10/2006 | Messina et al. ............... 424/93.7 |
| 2006/0251624 A1 | 11/2006 | Dezawa et al. |
| 2010/0034790 A1 * | 2/2010 | Dezawa et al. ............ 424/93.21 |

FOREIGN PATENT DOCUMENTS

EP 1 479 767 A 11/2004

OTHER PUBLICATIONS

Dezawa, et al., "Specific Induction of Neuronal Cells from Bone Marrow Stromal Cells and Application for Autologous Transplantation," *J Clin Invest* 113(12):1701-1710 (2004).
Dezawa, et al., "Treatment of Neurodegenerative Diseases Using Adult Bone Marrow Stromal Cell-Derived Neurons," *Expert Opinion on Biological Therapy* 5(4):427-435 (2005).
Ellisen, et al., "TAN-1, the Human Homolog of the *Drosophila* Notch Gene, is Broken by Chromosomal Translocations in T Lymphoblastic Neoplasms," *Cell* 66:649-661 (1991).
Munoz, et al., "Human Stem/Progenitor Cells from Bone Marrow Promote Neurogenesis of Endogenous Neural Stem Cells in the Hippocampus of Mice," *PNAS USA* 102(50): 18171-18176 (2005).
Mimura, et al., "Behavioral and Histological Evaluation of a Focal Cerebral Infacrction Rat Model Transplanted With Neurons Induced from Bone Marrow Stromal Cells," *J Neuropathol Exp Neurol* 64:1108-1117 (2005).

* cited by examiner

*Primary Examiner* — Laura Schuberg
(74) *Attorney, Agent, or Firm* — Pasternak Patent Law; Dahna S. Pasternak; Sean M. Brennan

(57) ABSTRACT

Disclosed herein are methods and compositions for the use of marrow adherent stem cells and their descendents; e.g., bone marrow-derived neural regenerating cells; in the treatment of various neurodegenerative disorders. In certain embodiments, bone marrow-derived neural regenerating cells transplanted to sites of neural degeneration stimulate growth and/or survival of host neurons.

21 Claims, 9 Drawing Sheets

METHODS AND COMPOSITION FOR TREATING NEURAL DEGENERATION

CROSS REFERENCE TO RELATED APPLICATIONS

This application claims priority to U.S. provisional application No. 60/964,763, filed on Aug. 15, 2007 and to U.S. provisional application No. 61/000,972, filed on Oct. 30, 2007, and to U.S. provisional application No. 61/005,181, filed on Dec. 3, 2007, and to U.S. provisional application No. 61/125,991, filed on Apr. 30, 2008; the disclosures of which are incorporated by reference in their entireties for all purposes.

STATEMENT REGARDING FEDERAL SUPPORT

Not applicable.

FIELD

The methods and compositions disclosed herein are in the field of neural degeneration (e.g., neurodegenerative diseases) and treatments therefor.

BACKGROUND

Neurodegenerative diseases such as, for example, Parkinson's disease, Alzheimer's disease and amyotrophic lateral sclerosis (ALS) are characterized by the death and/or degeneration of neurons and neural tissue. Because terminally differentiated neurons are limited in their ability to proliferate, a possible method of treatment for conditions characterized by neural degeneration is to provide new neural cells to replace those lost by cell death or injury. To this end, neural cell transplantation has been attempted in animal experiments using embryonic or adult neural stem cells, ES cells and embryonic neural cells. However, such uses face major hurdles against their application in humans. The use of embryonic stem cells or neural cells is beset with ethical issues, and the question of guaranteeing a stable supply is also a concern. Although the demonstrated ability of ES cells to differentiate is currently attracting much attention, the cost and labor required to induce differentiation to specific cell types, and the risk of forming teratoid tumors after transplantation, are factors impeding stable application of this technology. On the other hand, patients undergoing transplantation of adult neural stem cells are exposed to a tremendous risk and burden, since these cells are found in a very limited core section of the central nervous system (i.e., deep in the brain) and thus must be extracted by craniotomy. Finally, attempts to treat neural degeneration and nerve injury by transplantation of other types of pluripotent cells, such as hematopoietic stem cells, have met with limited success, due to the difficulty of controlling the differentiation of the transplanted cells.

As a result of the aforementioned difficulties associated with the use of embryonic cells, adult neural stem cells and various adult pluripotent cells for the treatment of neurodegenerative diseases, new methods and compositions for treatment of neurodegenerative diseases are required.

SUMMARY

New methods of treatment for neurodegenerative disease, as disclosed herein, make use of cells which, when transplanted to sites of neural degeneration, act on surrounding cells by inducing surrounding non-neural cells to differentiate into neurons or neural tissue, by facilitating recovery of damaged or dying neural cells, and/or by promoting survival of host neurons. Additional new treatment method involve transplantation of cells that inhibit the action of host cells that mediate or otherwise participate in the processes of neuronal cell death and/or degeneration.

Accordingly, disclosed herein are methods for neural regeneration which can be used, for example, in the treatment of neural degeneration and neurodegenerative diseases. Such methods include transplantation of bone marrow-derived cells, that have been induced to acquire certain properties that facilitate neural regeneration, at or near the site of neural degeneration. Thus, in certain embodiments, the disclosed methods for neural regeneration and treatment of neural degeneration involve transplanting bone marrow adherent stromal cells or bone marrow-derived neural regenerating cells at or near a site of neural degeneration.

The disclosed methods and compositions are useful for treatment of degeneration in either the central nervous system or the peripheral nervous system. For example, the disclosed methods and compositions can be used for treatment of central nervous system disorders such as, for example, Parkinson's disease, amyotrophic lateral sclerosis (ALS), stroke and Alzheimer's disease. Neural degeneration or physical injury to neurons in the peripheral nervous system can also be treated using the disclosed methods and compositions.

In certain embodiments bone marrow-derived neural regenerating cells are descended from bone marrow stromal cells (also known as marrow adherent stromal cells) that have been modified so that they express the amino acid sequence of the Notch intracellular domain (NICD). In certain embodiments, bone marrow stromal cells are transfected with a nucleic acid or polynucleotide comprising sequences encoding the Notch intracellular domain, and the bone marrow-derived neural regenerating cells descended from said transfected cells are used for transplantation. In certain embodiments the Notch intracellular domain consists of amino acids 1703-2504 of the human Notch-1 protein. Ellison et al. (1991) *Cell* 66:649-661.

Without wishing to be bound by any particular theory, in certain embodiments the transplanted bone marrow adherent stromal cells and bone marrow-derived neural regenerating cells exert their regenerative effect by supporting the growth of host nerve fibers (e.g., axons) at or near the site of neural degeneration. In other embodiments, the transplanted bone marrow adherent stromal cells and bone marrow-derived neural regenerating cells exert their regenerative effect by promoting survival of host neurons at or near the site of neural degeneration. These regenerative effects can result from the secretion of one or more trophic factors by the transplanted cells. Alternatively, regeneration can result from production of one or more extracellular matrix molecule(s), by the transplanted cells, that facilitate growth and/or survival of host neurons. Regenerative effects can also result from the combined action of secreted diffusible factors (e.g., growth factors) and non-diffusible factors (e.g., extracellular matrix).

Thus, the disclosure includes, but is not limited to the following numbered embodiments:

1. A method for treating neural degeneration, wherein the method comprises transplanting marrow adherent stromal cells or bone marrow-derived neural regenerating cells at or near a site of neural degeneration.

2. The method of embodiment 1, wherein the site of neural degeneration is in the central nervous system.

3. The method of embodiment 1, wherein the site of neural degeneration is in the peripheral nervous system.

4. The method of embodiment 2, wherein the neural degeneration is associated with Parkinson's Disease.

5. The method of embodiment 1, wherein the bone marrow-derived neural regenerating cells are descendents of bone marrow stromal cells that have been transfected with a polynucleotide comprising sequences encoding the Notch intracellular domain (NICD).

6. The method of embodiment 5, wherein the NICD consists of amino acids 1703-2504 of the Notch-1 protein.

7. The method of embodiment 1, wherein the bone marrow adherent stromal cells or the bone marrow-derived neural regenerating cells support growth of host nerve fibers at or near the site of neural degeneration.

8. The method of embodiment 7, wherein the nerve fibers are axons.

9. The method of embodiment 1, wherein the bone marrow adherent stromal cells or the bone marrow-derived neural regenerating cells promote survival of host neurons at or near the site of neural degeneration.

10. The method of embodiment 1, wherein the bone marrow adherent stromal cells or the bone marrow-derived neural regenerating cells secrete one or more trophic factors.

11. A method for neural regeneration, wherein the method comprises transplanting bone marrow adherent stromal cells or bone marrow-derived neural regenerating cells at or near a site of neural degeneration.

12. The method of embodiment 11, wherein the site of neural degeneration is in the central nervous system.

13. The method of embodiment 11, wherein the site of neural degeneration is in the peripheral nervous system.

14. The method of embodiment 12, wherein the neural degeneration is associated with Parkinson's Disease.

15. The method of embodiment 11, wherein the bone marrow-derived neural regenerating cells are descendents of bone marrow stromal cells that have been transfected with a polynucleotide comprising sequences encoding the Notch intracellular domain (NICD).

16. The method of embodiment 15, wherein the NICD consists of amino acids 1703-2504 of the Notch-1 protein.

17. The method of embodiment 11, wherein the bone marrow adherent stromal cells or the bone marrow-derived neural regenerating cells support growth of host nerve fibers at or near the site of neural degeneration.

18. The method of embodiment 17, wherein the nerve fibers are axons.

19. The method of embodiment 11, wherein the bone marrow adherent stromal cells or the bone marrow-derived neural regenerating cells promote survival of host neurons at or near the site of neural degeneration.

20. The method of embodiment 11, wherein the bone marrow adherent stromal cells or the bone marrow-derived neural regenerating cells secrete one or more trophic factors.

21. A method for providing trophic support to damaged neural tissue in a host, wherein the method comprises transplanting marrow adherent stromal cells or bone marrow-derived neural regenerating cells at or near a site of neural degeneration in the host.

22. The method of embodiment 21, wherein said trophic support promotes survival of host neural cells.

23. The method of embodiment 21, wherein said trophic support prevents death of host neural cells.

24. The method of embodiment 23, wherein said cell death is by apoptosis.

25. The method of embodiment 21, wherein said trophic support enhances function of host neural cells.

26. The method of embodiment 21, wherein said trophic support stimulates growth of host neural cells.

27. The method of embodiment 26, wherein outgrowth of nerve fibers is stimulated.

28. The method of embodiment 27, wherein the nerve fibers are axons.

29. The method of embodiment 27, wherein the nerve fibers are dendrites.

30. The method of embodiment 26, wherein new synapses are formed.

31. The method of embodiment 21, wherein said trophic support facilitates recruitment of host stem cells to the damaged tissue.

32. The method of embodiment 21, wherein the damaged neural tissue is in the central nervous system.

33. The method of embodiment 21, wherein the damaged neural tissue is in the peripheral nervous system.

34. The method of embodiment 32, wherein the damaged neural tissue is associated with Parkinson's Disease.

35. The method of embodiment 21, wherein the bone marrow-derived neural regenerating cells are descendents of marrow adherent stromal cells that have been transfected with a polynucleotide comprising sequences encoding the Notch intracellular domain (NICD).

36. The method of embodiment 35, wherein the NICD consists of amino acids 1703-2504 of the Notch-1 protein.

37. The method of embodiment 21, wherein the marrow adherent stromal cells or the bone marrow-derived neural regenerating cells secrete one or more trophic factors.

38. The method of embodiment 37, wherein the marrow adherent stromal cells or the bone marrow-derived neural regenerating cells secrete one or more of vascular endothelial growth factor, hepatocyte growth factor, bone morphogenetic protein 4, Dkk-1, fibroblast growth factor-7, heparin-binding epidermal growth factor-like growth factor, interleukin-6, interleukin-8, monocyte chemoattractant protein-1, matrix metalloproteinase-1, platelet-derived growth factor AA and transforming growth factor alpha.

On the right side of the Figure, the effect of co-culture with MASCs and NRCs is assessed. The fourth bar from the right shows relative number of neurons in a positive control culture grown in complete neuronal medium ("Compl. NB") without co-culture. The three right-most bars show results obtained with neurons that had been cultured in serum-free αMEM. The third bar from the right shows results for neurons that were not co-cultured; the second bar from the right shows results for neurons that had been co-cultured with 5,000 D31

MASCs; and the rightmost bar shows results for neurons that had been co-cultured with 5,000 D31 NRCs.

Figure 3:
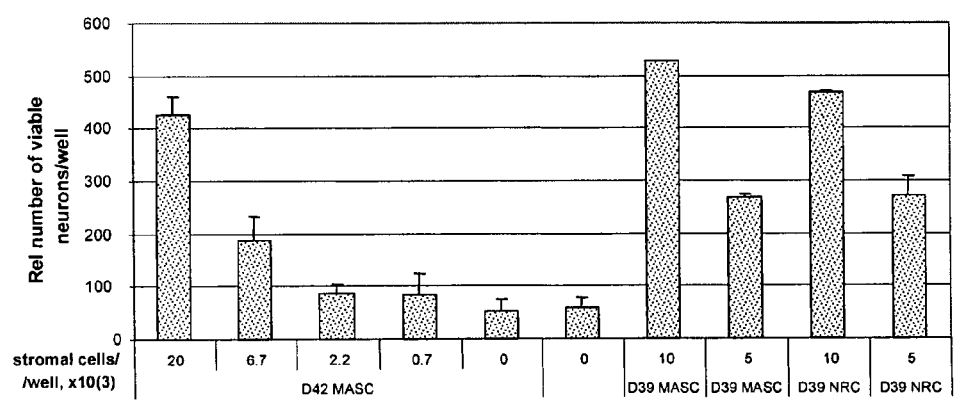

FIG. 3 shows relative numbers of surviving neurons, based on assay of intracellular LDH, in primary rat cortical neurons that had been co-cultured with MASCs and NRCs. The leftmost five bars show results from a titration of MASCs from Donor 42 (D42), co-cultured with cortical neurons in serum-free αMEM. Numbers of D42 MASCs ($\times 10^{-3}$) placed into co-culture with the neurons are shown along the abscissa.

On the right side of the Figure, the effect of co-culture with MASCs and NRCs in serum-free αMEM is assessed. The fifth bar from the right shows results for neurons that were not co-cultured; the third and fourth bars from the right shows results for neurons that had been co-cultured with 5,000 or 10,000 D39 MASCs, respectively; and the rightmost bar and the second bar from the right shows results for neurons that had been co-cultured with 5,000 and 10,000 D39 NRCs, respectively.

Figure 4:
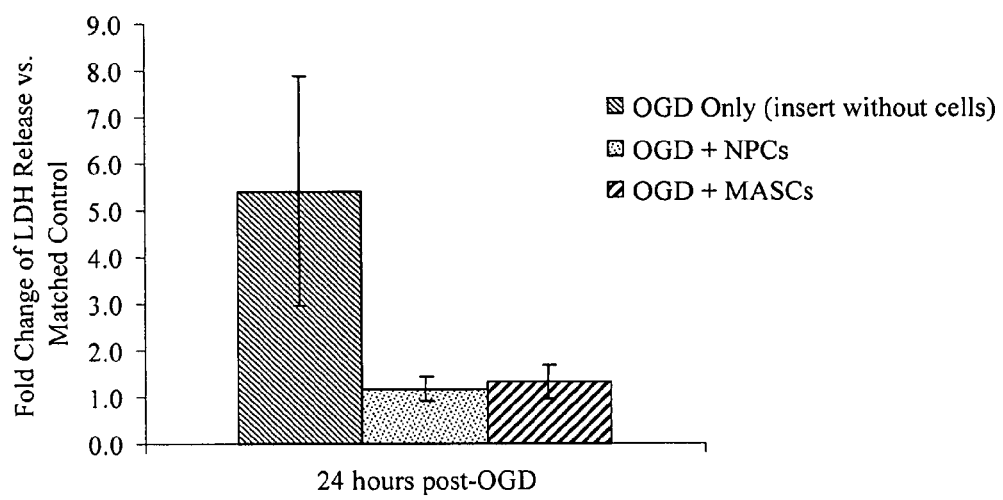

FIG. 4 shows cell damage (expressed as fold change in LDH release compared to controls) in cultures of primary neurons subjected to oxygen/glucose deprivation (OGD) with and without subsequent co-culture with marrow adherent stromal cells (MASCs) or neural regenerating cells (NRCs). The graph shows data pooled from results obtained with cells from six donors. For all samples, $p<0.05$ vs. OGD only.

Figure 5:
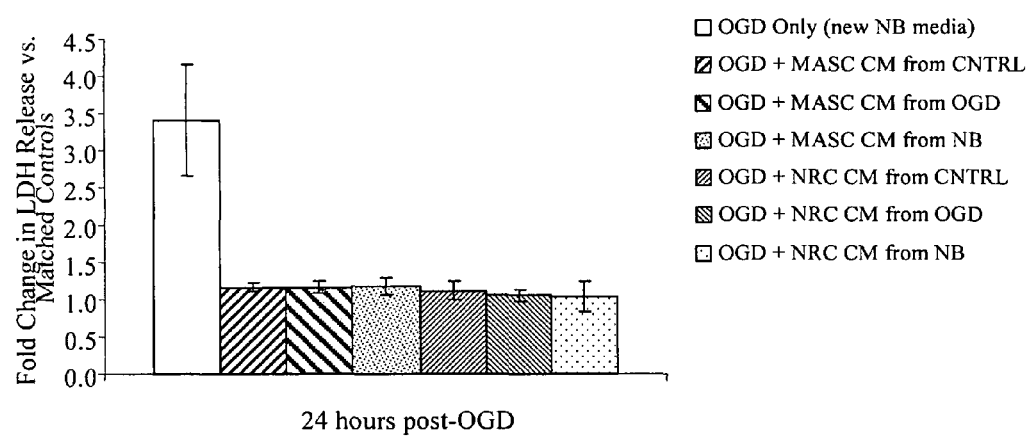

FIG. 5 shows cell damage (expressed as fold change in LDH release compared to controls) in cultures of primary neurons subjected to oxygen/glucose deprivation (OGD) with and without subsequent co-culture with various types of conditioned medium (CM) from marrow adherent stromal cells (MASCs) or neural regenerating cells (NRCs). "CM from NB" refers to conditioned medium from donor cells (MASCs or NRCs) cultured in neuronal medium; "CM from OGD" refers to conditioned medium from donor cells that had been cultured in neuronal medium which itself had been conditioned by OGD-injured neurons; "CM from CNTRL" refers to conditioned medium from donor cells that had been cultured in neuronal medium which itself had been conditioned by non-injured neurons. For all samples, $p<0.05$ vs. OGD only.

Figure 6:
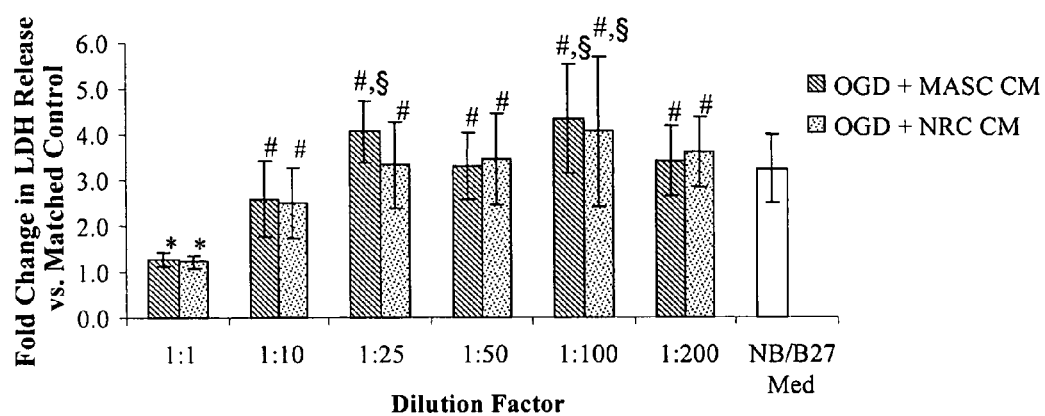

FIG. 6 shows cell damage (expressed as fold change in LDH release compared to controls) in cultures of primary neurons subjected to oxygen/glucose deprivation (OGD) and subsequently co-cultured with various dilutions of conditioned medium (CM) from marrow adherent stromal cells (MASCs) or neural regenerating cells (NRCs). Conditioned medium was diluted 1:1, 1:10, 1:25, 1:50, 1:100 or 1:200, as indicated. Control neurons (NB/B27 Med) were co-cultured with neuronal medium (see Example 7 for composition). The ability of donor cell-conditioned medium to rescue injured neurons is dose dependent. *$p<0.05$ vs. OGD Only; #$p<0.05$ vs. CM 1:1; §$p<0.05$ vs. CM 1:10; Mean±SD.

Figure 7:
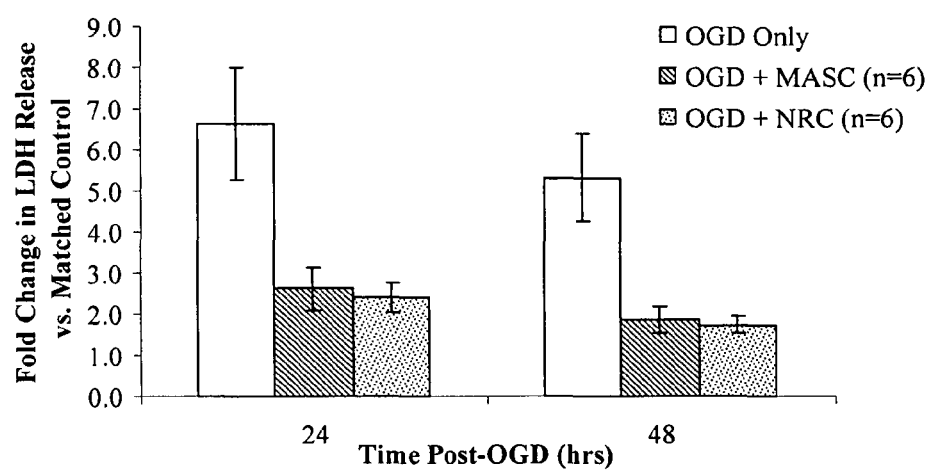

FIG. 7 shows cell damage (expressed as fold change in LDH release compared to controls) in rat hippocampal slices subjected to oxygen/glucose deprivation (OGD) with and without subsequent co-culture with marrow adherent stromal cells (OGD+MASC) or neural regenerating cells (OGD+NRC). The graph shows results of co-culture of hippocampal slices with MASCs or NRCs from six donors. For all samples, $p<0.05$ vs. OGD only.

Figure 8:
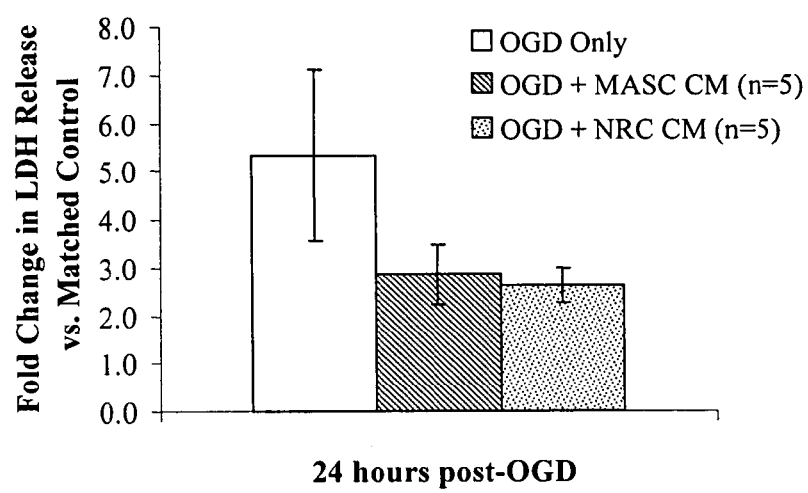

FIG. 8 shows cell damage (expressed as fold change in LDH release compared to controls) in rat hippocampal slices subjected to oxygen/glucose deprivation (OGD) with and without subsequent co-culture (for 24 hours) with conditioned medium (CM) from marrow adherent stromal cells (MSC) or neural regenerating cells (NRC). For all samples, $p<0.05$ vs. OGD only.

Figure 9:
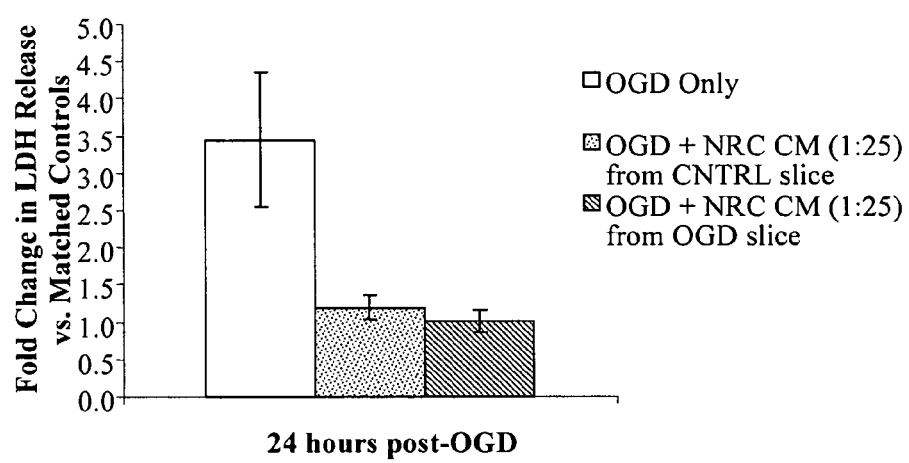

FIG. 9 shows cell damage (expressed as fold change in LDH release compared to controls) in cultures of primary neurons subjected to oxygen/glucose deprivation and then further cultured for 24 hours in neuronal medium (OGD only; left bar), diluted conditioned medium from NRCs that had been cultured for 48 hours in the presence of hippocampal slices (OGD+NRC CM (1:25) from CNTRL slice; center bar) or diluted conditioned medium from NRCs that had been cultured for 48 hours in the presence of OGD-damaged hippocampal slices (OGD+NRC CM (1:25) from OGD slice; right bar). *$p<0.05$ vs. OGD only group; #$p<0.05$ OGD+NRC CM from CNTRL slice.

DETAILED DESCRIPTION

The terms "transplant," "graft" and "engraft" are used interchangeably to refer to the placement of exogenous cells into a particular location in a subject or tissue. "Autologous" transplantation refers to transplantation of a subject's own cells into the subject (for example, cells being removed from one site in a subject and transferred to a different site in the same subject, with or without additional treatment of the cells between removal and transfer). "Allogeneic" transplantation refers to transfer of cells to a subject, said cells having been obtained from a different individual.

The terms "bone marrow stromal cells," "marrow adherent stromal cells," "marrow adherent stem cells," "marrow stem cells," "bone marrow stem cells," "mesenchymal stem cells" and "MASCs" refer to mitotic, pluripotent cells, obtained from bone marrow that, in the course of normal development, are capable of giving rise to a number of differentiated cell types such as, for example, osteocytes, and cells normally found in connective tissue including, but not limited to, chondrocytes and adipocytes. MASCs can be human cells or cells from other mammals or vertebrates.

The terms "neural regenerating cell," "neuronal regenerating cell," "NRC" and "bone marrow-derived neural regenerating cell" are used interchangeably to refer to mitotic cells, descended from marrow adherent stromal cells, that have the capability to promote growth and survival, and/or to prevent apoptosis and death, of injured neural cells, such as neurons, glia, and their precursors. They are thus distinct from primary neuronal precursor cells, such as can be obtained from fetuses or adult tissues such as the hippocampus and the periventricular subependymal zone. NRCs can be human cells or cells from other mammals or vertebrates.

A "trophic factor" or "growth factor" is any molecule that promotes regeneration, growth and/or survival of a damaged cell (e.g. a neuron, astrocyte or oligodendrocyte). Such factors may be secreted by cells other than the damaged cell; for example, by marrow adherent stromal cells or neural regenerating cells that have been transplanted to a site of neural damage, or by descendents of said transplanted cells.

Degenerative disorders of the nervous system, in which reconstruction is not an option, include a variety of different conditions with a high incidence rate in the population, including injury-induced spinal damage, cerebrovascular impairment, glaucoma (which can lead to blindness), and neurodegenerative conditions such as Parkinson's disease, ALS and Alzheimer's disease. Thus, the neuroregenerative methods and compositions disclosed herein fulfill an urgent human health need.

ALS (amyotrophic lateral sclerosis) is a condition in which cell death of spinal cord motor neurons leads to loss of function of nerves which control muscular contraction, thereby preventing movement of muscles throughout the body (including muscles involved in respiration) and leading to death of the patient within 2-3 years after onset. No effective treatment for ALS currently exists. The availability of cells, from one's own bone marrow, which support the regeneration of acetylcholinergic neurons would allow autologous transplantation, and this would offer a major benefit that might even serve as a cure for ALS.

Alzheimer's disease is a condition, characterized by dementia, in which cell death in the central nervous system is accompanied by intracellular neurofibrillary tangles and extracellular plaques containing deposits of beta-amyloid protein. No treatment is available.

Parkinson's disease is characterized by the death of a group of neurons that synthesize the neurotransmitter dopamine (DA). These neurons are located in the substantia nigra pars compacta of the midbrain and send axons to forebrain areas, such as caudate nucleus and putamen which are collectively referred to as the striatum. DA in the striatum is critically important to the control of movement and loss of DA in this brain area results in resting tremor, bradykinesia, difficulty in initiating movement and postural deficiencies. This leaves patients incapable of initiating and controlling movements in a normal way. The disease is chronic and progressive, and there is presently no cure for Parkinson's disease, nor is there any therapy that inhibits or reverses the loss of DA neurons.

The aforementioned diseases, and other diseases or syndromes characterized by neural degeneration, can be treated by providing new neural cells at or near sites of neural degeneration, by stimulating the growth and/or regeneration of damaged or dying neural cells, and/or by promoting the survival of damaged or dying neural cells. Accordingly, the methods and compositions disclosed herein can be used for treatment of any type of neural degeneration or neural injury, including but not limited to, Parkinson's disease, Alzheimer's disease and ALS.

Sites of neural degeneration can be identified anatomically, or may be known by virtue of the pathology of the disease being treated.

Moreover, the applications of this technology are not limited to the field of clinical treatment, but are also useful in the area of engineering of artificial organs and the like, which is expected to be an important field of development in the future. For example, production of neural cells and/or neural regenerating cells on a cell culturing level will facilitate creation of hybrid artificial organs and the like.

The present disclosure provides methods and compositions for, inter alia, treating neurodegenerative disorders by transplanting, at or near a site of neural degeneration or nerve injury, either marrow adherent stromal cells or bone marrow-derived neural regenerating cells (i.e., cells descended from marrow adherent stromal cells that have been induced to acquire an enhanced capacity to induce growth, survival and/or regeneration of damaged neural cells). Bone marrow stromal cells are easily extracted by bone marrow aspiration on an outpatient basis, and due to their highly proliferative nature they can be cultured in large amounts within a relatively short period. Moreover a further advantage of their use as starting material for the presently-disclosed methods and compositions is that they allow autologous transplantation to be carried out (i.e., new nerves and neural tissue are formed as a result of transplanting cells derived from the patient's own bone marrow stem cells). The consequent lack of immunological rejection dispenses with the need for administering immunosuppressants, thus enabling safer treatment. Furthermore, since bone marrow stem cells can be obtained from a bone marrow bank, this method is also advantageous from a supply standpoint.

Marrow adherent stromal cells are obtained, for example, from bone marrow aspirates by culturing for three days in α-MEM+10% FBS+L-Glutamine, then aspirating away non-adherent cells. See Example 1 for details.

In certain embodiments, bone marrow-derived neural regenerating cells are obtained by methods comprising transfection of marrow adherent stromal cells with a polynucleotide comprising a sequence encoding a Notch intracellular domain (NICD) as described, for example, in US Patent Application Publication No. 2006-0166362 (Jul. 27, 2006), the disclosure of which is incorporated by reference, and Dezawa et al. (2004) *J. Clin. Invest.* 113:1701-1710, the disclosure of which is incorporated by reference. In additional embodiments, such cells are obtained as described in US Patent Application Publication No. 2006-0251624 (Nov. 9, 2006), the disclosure of which is incorporated by reference. Alternatively, such cells can be obtained as described in US Patent Application Publication No. 2003-0003090 (Jan. 2, 2003), the disclosure of which is incorporated by reference. An exemplary method for obtaining neural regenerating cells is described in Example 2, infra.

The cells described herein may be suspended in a physiologically compatible carrier for transplantation. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, Hank's balanced salt solution+/−glucose (HBSS), and multiple electrolyte solutions such as Plasma-Lyte™ A (Baxter).

Transplantation, of either marrow adherent stromal cells or bone marrow-derived neural regenerating cells, is accomplished by any method known in the art, including, for example, injection of said cells or surgical implantation. Cells can be transplanted by themselves, in a buffer or suspension, as a "graft forming unit (GFU)" or in association with a matrix or support material. See, for example, U.S. Pat. No. 6,989,271 and U.S. Patent Application Publication No. 2006-0216276, both of which disclosures are incorporated by reference.

The volume of cell suspension administered to a patient will vary depending on the site of implantation, treatment goal and amount of cells in solution. Typically the amount of cells administered to a patient will be a "therapeutically effective amount." As used herein, a therapeutically effective amount refers to the number of transplanted cells which are required to effect treatment of the particular disorder. For example, where the treatment is for Parkinson's disease, transplantation of a therapeutically effective amount of cells will typically produce a reduction in the amount and/or severity of the symptoms associated with that disorder, e.g., rigidity, akinesia and gait disorder, and optionally produce an increase in tyrosine hydroxylase-expressing nerve fibers.

The cells may be implanted within the parenchyma of the brain, in the space containing cerebrospinal fluids, such as the sub-arachnoid space or ventricles, or extaneurally. As used herein, the term "extraneurally" is intended to indicate regions of the patient which are not within the central nervous system or peripheral nervous system, such as the celiac ganglion or sciatic nerve. "Central nervous system" is meant to include all structures within the dura mater.

Typically, the cells are administered by injection into the brain of the subject. The exact size needle will depend on the species being treated, but preferably the needle should not be bigger than 1 mm diameter in any subject.

The disclosed methods and compositions for neural regeneration can be used for treatment of neurodegeneration in both the central and peripheral nervous systems. Central nervous system disorders suitable for treatment as disclosed herein include, for example, stroke, Parkinson's disease, Alzheimer's disease, ALS and various types of spinal cord injury or brain trauma. Disorders of the peripheral nervous system suitable for treatment as disclosed herein include, for example, physical damage to peripheral nerves; drug-induced, diabetic or spontaneous neuropathy; neuropathic pain; sensory or motor defects; dyskinesia; hereditary motor and sensory neuropathies; infectious polyneuropathies and inflammatory neuropathies.

In certain embodiments, the transplanted cells, which comprise bone marrow adherent stromal cells and/or their descendents, undergo further differentiation after transplantation to become neurons (e.g., cholinergic neurons or dopaminergic neurons) and/or glial cells. Such differentiated cells, in certain embodiments, nevertheless retain certain immunological markers characteristic of bone marrow stromal cells.

In additional embodiments, the transplanted cells induce recovery of damaged neurons and/or glial cells. Such recovery can be mediated by cell-cell contact (between the transplanted cells and the damaged neural cells) or by secretion of one or more factors (diffusible or non-diffusible) by the transplanted cells that rescue the damaged neural cells. Rescue of astrocytes and/or microglia can be important in the treatment a number of neurological disorders (e.g., ALS), as these cell types can, in turn, secrete factors that support the survival and growth of motor neurons.

In further embodiments, the transplanted cells induce endogenous cells (such as, for example, fibroblasts, mesenchymal cells, stromal cells, endothelial cells and/or neural stem cells) to differentiate into new neurons and/or glial cells. Such differentiation can be mediated by cell-cell contact (between the transplanted cells and one or more endogenous cells) or by secretion of factors which induce differentiation of endogenous cells.

In yet additional embodiments, the transplanted cells secrete trophic factors which induce the growth of existing neural processes to sites of neural degeneration, thereby reversing neural degeneration and/or restoring neural tissue lost by degeneration.

Certain examples below show the use of the disclosed methods and compositions in 6-hydroxydopamine (6-OHDA)-treated rat brains, which is a well-known and well-accepted model of Parkinson's disease. In this model, 6-OHDA causes the progressive loss of dopaminergic neurons, which mimics the pathology of Parkinson's disease. These particular results indicate that bone marrow-derived neural regenerating cells are able to rejuvenate damaged or diseased dopaminergic neurons and, thus, can be used as a cell therapy for Parkinson's Disease and other types of neural degeneration. Additional examples show that either marrow adherent stromal cells or neural regenerating cells are capable of reversing damage caused by oxygen/glucose deprivation in cultured neurons and hippocampal slices. Additional examples describe the identification and quantitation of a number of trophic factors secreted by marrow adherent stromal cells and neural regenerating cells.

EXAMPLES

Example 1

Preparation of Marrow Adherent Stromal Cells (MASCs)

Bone marrow aspirates, obtained from human donors, were divided into 12.5 ml aliquots in 50 ml tubes, and 12.5 ml of growth medium (10% FBS in αMEM, supplemented with penicillin/streptomycin and 2 mM L-glutamine) was added to each tube. The contents of the tubes were mixed by inversion and the tubes were centrifuged at 200×g for 8 minutes. The upper, clear phase was discarded, the volume of the lower phase was adjusted to 25 ml with fresh growth medium, and the tubes were again mixed and centrifuged. The upper layer was again removed. The volume of the lower phase in each tube was again adjusted to 25 ml and the contents of all tubes was pooled in a 250 ml tube. After determination of cell concentration by Trypan Blue exclusion and determination of nucleated cell count, cells were plated in T225 flasks, in 40 ml per flask of growth medium at a density of $100 \times 10^6$ total nucleated cells per flask. The flasks were incubated at 37° C. for 3 days in a $CO_2$ incubator, during which time the MASCs attached to the flask.

After 3 days, unattached cells were removed by rocking the flasks and withdrawing the culture medium. Each flask was washed three times with 40 ml of αMEM supplemented with penicillin/streptomycin; then 40 ml of prewarmed (37° C.) growth medium was added to each flask and the cells were cultured at 37° C. in a $CO_2$ incubator. During this time, the medium was replaced with 40 ml of fresh growth medium every 3-4 days, and cells were monitored for growth of colonies and cell density.

When the cultures achieved 25-30% confluence (usually 10,000-20,000 cells per colony and within 10-14 days), the MASCs (passage M0) were harvested for further passage. MASCs were harvested from up to 10 T-225 flasks at a time. Medium was removed from the flasks and the adherent cells were rinsed with 20 ml of DPBS w/o Ca/Mg (DPBS-/-, HyClone) 2 times. Ten ml of 0.25% Trypsin/EDTA (Invitrogen, Carlsbad, Calif.) was added to each flask and flasks were incubated for approximately 5 min at room temperature. When cells had detached and the colonies had dispersed into single cells, the trypsin was inactivated by addition of 10 ml of growth medium followed by gentle mixing. The cell suspensions were withdrawn from the flasks, and pooled in 250 ml tubes. The tubes were subjected to centrifugation at 200×g for 8 minutes. The supernatants were carefully removed and the wet cell pellets were resuspended in growth medium to an estimated cell concentration of approximately $1 \times 10^6$ cells/ml. Viable cell count was determined and cells were plated in T225 flasks at a concentration of $2 \times 10^6$ cells per flask in growth medium (passage M1). Cells were grown for 3-5 days, or until 85-90% confluent, changing medium every 2 to 3 days. At 85-90% confluence, passage M1 cells were harvested by trypsinization and replated at $2 \times 10^6$ cells per T225 flask as described above, to generate passage M2 cultures. M2 cultures were fed fresh medium every three days, if necessary. When passage M2 cultures reached 85-90% confluence (usually within 3-5 days), they were either harvested for transfection to generate NRCs (Example 2 below) or frozen for future use (Example 3 below).

Example 2

Preparation of Neural Regenerating Cells (NRCs)

NRCs were made either directly from MASCs harvested from passage M2 cultures, or from passage M2 MASCs that had been frozen as described in Example 3, and thawed and revived as described in Example 4.

A. Preparation of Transfection Mixture

Neural regenerating cells were made by transfection of passage M2 MASCs with a plasmid encoding the Notch intracellular domain. The plasmid (pCI-Notch) comprised a pCI-neo backbone (Promega, Madison, Wis.) in which sequences encoding amino acids 1703-2504 of the human Notch-1 protein, which encode the intracellular domain, were introduced into the multiple cloning site. For each flask of MASCs, 5 ml of transfection mixture, containing 40 μg of plasmid and 0.2 ml of Fugene 6® solution, was used. To make the transfection mixture, the appropriate amount of Fugene® solution (depending on the number of flasks of cells to be transfected) was added to αMEM in a sterile 250 ml tube, using a glass pipette. The solution was mixed gently and incubated for 5 min at room temperature. The appropriate amount of plasmid DNA was then added dropwise to the Fugene®/αMEM mixture, gently mixed, and incubated for 30 min at room temperature.

Prior to the addition of pCI-Notch DNA to the Fugene®/MEM mixture, 5 ml was removed and placed into a 15 ml tube to which was added 40 ug of pEGFP plasmid. This solution was used to transfect one flask of cells, as a control for transfection efficiency.

B. Transfection

For transfection, passage M2 MASCs were harvested by trypsinization (as described in Example 1) and plated at a density of $2.5 \times 10^6$ cells in 40 ml of growth medium per T225 flask. When the cells reached 50-70% confluence (usually within 18-24 hours) they were prepared for transfection, by replacing their growth medium with 35 ml per flask of transfection medium (αMEM+10% FBS without penicillin/streptomycin).

Three hours after introduction of transfection medium, 5 ml of the transfection mixture (Section A above) was added to each T-225 flask by pipetting directly into the medium, without contacting the growth surface, followed by gentle mixing. A control T-225 flask was transfected with 40 μg of pEGFP plasmid, for determination of transfection efficiency.

After incubating cultures at 37° C. in transfection medium for 24 hours, the transfection medium was replaced with αMEM+10% FBS+penicillin/streptomycin.

C. Selection of Transfected Cells

Cells that had incorporated plasmid DNA were selected 48 hrs after transfection by replacing the medium with 40 ml per flask of selection medium (growth medium containing 100 μg/ml G-418). Fresh selection medium was provided 3 days, and again 5 days after selection was begun. After 7 days, selection medium was removed and the cells were fed with 40 ml of growth medium. The cultures were then grown for about 3 weeks (range 18 to 21 days), being re-fed with fresh growth medium every 2-3 days.

Approximately 3 weeks after selection was begun, when surviving cells began to form colonies, cells were harvested. Medium was removed from the flasks using an aspirating pipette and 20 ml of DPBS without $Ca^{2+}/Mg^{2+}$, at room temperature, was added to each flask. The culture surface was gently rinsed, the wash solution was removed by aspiration and the rinse step was repeated. Then 10 ml of prewarmed (37° C.) 0.25% Trypsin/EDTA was added to each flask, rinsed over the growth surface, and the flasks were incubated for 5-10 min. at room temperature. Cultures were monitored with a microscope to ensure complete detachment of cells. When detachment was complete, trypsin was inactivated by addition of 10 ml of growth medium per flask. The mixture was rinsed over the culture surface, mixed by pipetting 4-5 times with a 10 ml pipette, and the suspension was transferred into a sterile 50 ml conical centrifuge tube. Cells harvested from several flasks could be pooled in a single tube. If any clumps were present, they were allowed to settle and the suspension was removed to a fresh tube.

The cell suspensions were centrifuged at 200×g for 8 min at room temperature. Supernatants were removed by aspiration. Cell pellets were loosened by tapping the tube, about 10 ml of DPBS without $Ca^{2+}/Mg^{2+}$ was added to each tube and cells were resuspended by gently pipetting 4-5 times with a 10 ml pipette to obtain a uniform suspension.

D. Expansion of Transfected Cells

Cell number was determined for the suspension of transformed, selected cells and the cells were plated in T-225 flasks at $2 \times 10^6$ cells per flask (providing approximately 30% seeding of viable cells). This culture is denoted M2P1 (passage #1). M2P1 cultures were fed with fresh medium every 2-3 days, and when cells reached 90-95% confluence (usually 4-7 days after passage), they were harvested and replated at $2 \times 10^6$ cells per flask to generate passage M2P2. When M2P2 cultures reached 90-95% confluence, they were harvested for cryopreservation (Example 3) or for further assay.

Example 3

Cryopreservation

MASCs and NRCs were frozen for storage according to the following procedure. MASCs were typically frozen after passage M2, and NRCs were typically frozen after passage M2P2. Processing 4-5 flasks at a time, medium was aspirated from the culture flasks, 10 ml of 0.25% Trypsin/EDTA (at room temperature) was added to each flask, gently rinsed over the culture surface for no longer than 30 sec, and removed by aspirating. Then 10 ml of warmed (37° C.) 0.25% Trypsin/EDTA was added to each flask, rinsed over the growth surface, and the flasks were incubated for 5-10 min. at room temperature. Cultures were monitored by microscopic examination to ensure complete detachment of cells.

When detachment was complete, 10 ml of αMEM growth medium was added to each flask, rinsed over the culture surface, and detached cells were mixed by pipetting 4-5 times with a 10 ml pipette. The cell suspension was transferred into a sterile 250 ml conical centrifuge tube, and any large clumps of cells were removed. Cells harvested from 15-20 flasks were pooled into one 250 ml tube.

The tube was subjected to centrifugation at 200×g for 8 min at room temperature. The supernatant was removed by aspirating. The pellet was loosened by tapping the tube, and about 25 ml of DPBS (−/−) was added to each tube. Cells were resuspended by gently pipetting 4-5 times with a 10 ml pipette to obtain a uniform suspension. Any clumps in the suspension were removed by pipetting each sample through a sterile 70 μm sieve placed in the neck of a 50 ml tube.

Cell suspensions were pooled in a 250 ml centrifuge tube and any remaining clumps were removed. The final volume was adjusted to 200 ml with DPBS (−/−) and the sample was subjected to centrifugation at 200×g for 8 min at room temperature. The supernatant was removed by aspiration. The cell pellet was loosened by tapping, 20 ml of DPBS (−/−) was added to the tube and cells were resuspended by mixing well and gently pipetting with a 10 ml pipette. The final volume was adjusted with DPBS (−/−) to give an estimated concentration of approximately $0.5$-$1.0 \times 10^6$ cells/ml, usually about 4-5 ml per T225 flask harvested, or about 200 ml for a 40-flask harvest.

A viable cell count was conducted on the suspension, which was then subjected to centrifugation at 200×g for 8 minutes. The supernatant was aspirated, and the cell pellet was resuspended in cold Cryo Stor solution (BioLife Solutions, Bothell, Wash.) to a concentration of 12×10$^6$ cells/ml. One ml aliquots were dispensed into vials, which were sealed and placed at 4° C. in a Cryo Cooler. Vials were transferred into a CryoMed (Thermo Form a) freezer rack and frozen.

Example 4

Thawing and Recovery

Frozen cells (MASCs or NRCs) were stored in liquid nitrogen. When needed for experiments, they were quick-thawed and cultured as follows. A tube of frozen cells was placed in a 37° C. bath until thawed. The thawed cell suspension (1 ml) was immediately placed into 10 ml of growth medium and gently resuspended. The suspension was centrifuged at 200× g, the supernatant was removed, and cells were resuspended in growth medium to an estimated concentration of 10$^6$ cells/ml. Live cells were counted by Trypan Blue exclusion and cells were plated at a density of 2×10$^6$ cells per T225 flask. Cells were cultured at 37° C. in a $CO_2$ incubator for 3-4 days until cell growth resumed.

Example 5

Survival of Bone Marrow-Derived Neural Regenerating Cells Transplanted into Rat Brain Adult male athymic rats were stereotaxically implanted in the dorsolateral striatum with 38,000 bone marrow-derived neural regenerating cells, obtained essentially as described in Example 2. Rats were sacrificed at 2 h, 48 h and 14 d post-transplantation. Cell survival was determined by localizing the transplanted human cells in perfused sections, using immunocytochemistry for human nuclear (HuNu) antibody. Sections were counterstained with Nissl or hematoxylin-eosin to assess potential toxicity resulting from transplantation. Survival of transplanted cells was 14% at 5 hr, 12% at 48 hr and 9% at 14 days after transplantation. This is an excellent level of cell survival compared to many studies of fetal cell and neuroprogenitor cells grafts, in which survival of transplanted cells is in the range of ≤5%.

Example 6

Induction of Dopaminergic Neurons after Transplantation of Bone Marrow-Derived Neural Regenerating Cells in a Rat Model of Parkinson's Disease This example shows that, in a rat model of Parkinson's disease, transplantation of bone marrow-derived neural regenerating cells induces growth and regeneration of dopaminergic neurons. The physiological principles governing neuronal growth (e.g., neurite outgrowth), development, regeneration and aging have been extensively studied in the rat and found to be similar to those operating in humans. In particular, partial lesion of the nigrostriatal projection, which approximates the pathology of Parkinson's disease in humans, can be achieved in the rat by injection of 6-hydroxydopamine (6-OHDA) into the striatum.

In two independent experiments, rat brains were treated with 6-hydroxydopamine (6-OHDA); subsequently bone marrow-derived neural regenerating cells were transplanted at the lesion site in certain of the 6-OHDA-lesioned brains. Transplanted cells survived and remained tyrosine hydroxylase (TH)-negative, while at the same time inducing the growth of TH-positive (i.e., dopaminergic) nerve fibers toward the transplant site. Amphetamine-induced nuclear translocation of the c-fos protein, an indicator of dopamine release, was also observed in some cases. The results show the involvement of bone marrow-derived neural regenerating cells in restoration, regeneration and recruitment of dopaminergic neurons in the rat Parkinson's disease model.

A. Processing of Bone Marrow-Derived Neural Regenerating Cells for Transplantation Bone marrow-derived neural regenerating cells, prepared as described in Example 2 above, were frozen in liquid nitrogen until used. To thaw, frozen vials containing the cells were placed immediately into a 37° C. water bath and kept there until content completely thawed. Vials were promptly removed and cells were transferred into a 15 ml conical centrifuge tube containing 10 ml of cold growth medium (alpha-MEM+10% FBS). The preparations were centrifuged at 200×g in a swinging bucket rotor for 8 minutes at room temperature to form a pellet of cells. Supernatant was carefully removed and DPBS w/o $Ca^{2+}$—$Mg^{2+}$ was added to yield a final cell concentration of about 0.5×10$^6$ cells/ml. Cell counting was done at this step to obtain the precise cell count and to check viability. Cells were then centrifuged at 200×g for 8 minutes at room temperature. 1.4 ml of DPBS w/o $Ca^{2+}$—$Mg^{2+}$ was added to the pellet to re-suspend, and the cells transferred to a 1.5 ml tube. The sample was then centrifuged at 200×g for 8 minutes. Most of the buffer was removed, then the cells were quickly centrifuged again at 200×g for 1 minute and the remaining buffer was removed using a P-200 pipettor.

Pellet volume was then estimated and the final target volume was calculated using the following formula:

$$\text{Target Volume (}\mu\text{L)} = \frac{\text{Viable Cell Yield (cells)}}{\text{Required Cell conc. (cells/}\mu\text{L)}}$$

Cell counting was done to check the final concentration and viability prior to implantation. After cell grafting the remaining cells were also checked for cell number and viability in order to ensure quality of the implantation procedure.

B. Generation of 6-OHDA Lesions

In two independent experiments, 38 adult male Fisher 344 rats were unilaterally lesioned by injection of 6-OHDA into the right striatum. Rats were anesthetized using isoflurane and heads were subsequently fixed in a stereotaxic apparatus equipped with nose cones for continuous isoflurane anesthesia. Breathing and pain reflexes were continuously monitored. An incision was made at the midline of the skull, the skin was retracted and the injection needle set at zero at the bregma. The injections sites were marked for each set of coordinates and a burr hole was made. Injection co-ordinates were: A/P: +0.2, M/L: −3.0, DAT: −5.5.

The injection needle (10 µl Hamilton syringe, 26 G needle) was lowered into position at a rate of 1 mm/min. After reaching injection position, the needle was held in place for 4 minutes before starting injection. Injection was then initiated (injection solution: 0.2 mg/ml ascorbic acid and 16 µg 6-OHDA, injection volume: 2.8 µl, rate: 0.5 µl/min). After injection, the needle was held in place for another 4 minutes to allow for diffusion of injected solution from the injection site. The needle was then slowly removed (1 mm/min). The skin was sutured together with discontinuous stitches (at least 5) and the wound was treated with Fougera double antimicrobial ointment and LMX4 topical anesthetic to prevent infection and discomfort of the animal.

C. Cyclosporine Treatment

Daily subcutaneous injections of 10 mg/kg Cyclosporine A were given to prevent immune reaction against grafted cells. Sandimmune (50 mg/ml) was diluted in sterile saline 1:5 (to give a final concentration of 10 mg/ml) before injection. Injections were started 24 hours prior to cell grafting and given daily through the remainder of the experiment.

D. Transplantation

Seven days after treatment with 6-OHDA, bone marrow-derived neural regenerating cells were transplanted at the lesion sites. Transplantation was accomplished by stereotaxic injection of 0.5 µl of bone marrow-derived neural regenerating cell suspension, at various cell doses (6,000-21,000 cells/µl) in PBS, into the lesioned striatum in 19 rats. Nine control rats received no further treatment (lesion only group). Ten control rats received PBS at the same coordinates. Ten deposits were made around the lesion site, with two deposits in every needle track (co-ordinates: 1-2: A/P: +0.5, M/L: −2.5, D/V: −4.4/−5.8; 3-4: A/P: +0.5, M/L: −3.5, D/V: −4.8/−6.2; 5-6: A/P: 0.0, M/L: −3.0, D/V: −4.8/−6.2; 7-8: A/P: −0.3, M/L: −2.7, D/V: −4.2/−5.4; 9-10: A/P: −0.3, M/L: −3.8, D/V: −5.0/−6.2). Injection was done with 10 µl Hamilton syringes with 26 G needles (straight 30 degree angle tip). The injection protocol was changed to accommodate cell injections. Needles were held in place for 1 minute before and after injections. Injection parameters were: 0.5 µl/deposit, 1 µl/minute rate. New burr holes for the extra injection sites were established at the beginning of the surgery. Grafted cell numbers were: 6,000 cells/graft (n=3), 8,000 cells/graft (n=3), 12,000 cells/graft (n=4) and 21,000 cells/graft (n=3).

E. Euthanasia

Three weeks after transplantation, rats were sacrificed and their brains were examined for the presence of dopaminergic (i.e., TH-positive) neurons. Two hours before sacrifice, IP injection of DL-amphetamine (5 mg/kg) was given to the rats to induce c-fos expression in striatal target neurons that receive projections from dopaminergic axons. Rats were then overdosed with pentobarbital. Corneal and toe pinch reflexes were checked to make sure anesthesia was adequate before proceeding to intracardiac perfusion with saline (400 ml) followed by 4% paraformaldehyde (400 ml).

F. Tissue Processing

After intracardiac perfusion with paraformaldehyde, brains were removed, blocked and postfixed overnight, then transferred into 10%, 20% and 30% sucrose solutions consecutively after the tissue had sunk in each solution. Frozen coronal sections of 40 µm thickness were collected from each brain and kept in cryoprotective solution at −20° C. until stained.

G. Immunocytochemistry/Staining

Immunoreactivity for tyrosine hydroxylase (TH), the enzyme that catalyzes the rate-limiting step in dopamine synthesis, was used as a test for the presence of dopaminergic neurons. Two procedures were used. In the first, frozen sections were washed three times in PBS, then blocked in PBS containing 0.3% Triton X100 and 3% normal goat serum (blocking solution) for 1 hr at room temperature. Primary antibody was then added (Rabbit anti-TH, Chemicon, 1:1000) to the blocking solution and incubation was continued overnight at room temperature on an orbital shaker. Sections were then washed in PBS briefly and incubated with secondary antibody (biotinylated goat anti-rabbit, 1:500) for 2 hours at room temperature. DAB staining was done using the Vectastain ABC kit and DAB substrate kit (Vector Laboratories) following the manufacturer's protocol.

In the second procedure, frozen sections obtained from the striatum were washed 3 times in Tris-buffered saline (TBS), incubated for 15 min in 0.3% $H_2O_2$ in TBS, blocked for 20 min at room temperature in 10% normal goat serum (NGS), 0.5% Triton x-100 (TX-100) in TBS and briefly washed in TBS/0.1% TX-100. Sections were then incubated overnight at room temperature (RT) on an orbital shaker with 1:2000 polyclonal rabbit anti-TH antibody (Chemicon) in 1% NGS and 0.3% TX-100 in TBS. Sections were then washed briefly in TBS/0.1% TX-100, and incubated for 2.5 hours on room temperature with biotinylated goat anti-rabbit antibody (Vector Laboratories) diluted 1:500 in 1% NGS and 0.1% TX-100 in TBS, followed by incubation in avidin-peroxidase conjugate (Vectastain ABC Elite, Vector Laboratories) in TBS for 2 h. Visualization was done with DAB (20 mg/ml), 0.8% nickel sulfate, 0.005% $H_2O_2$ in 50 mM sodium acetate, 10 mM imidazole buffer (pH 7.0). Several washes with 0.1% TX-100 in TBS were performed between each step.

Surviving bone marrow-derived neural regenerating cells in tissue sections were detected by staining for human nuclear mitotic apparatus protein or nuclear matrix protein (hNuMA). Following antigen retrieval by incubation in 10 mM sodium citrate buffer, pH 8.5, at 80° C. for 30 min, striatal sections were washed three times in PBS and blocked for one hour at room temperature in 5% NGS, 5% BSA in 1% TX-100 in PBS. Sections were incubated for 48 h at 4° C. in mouse monoclonal anti-hNuMA antibody (Calbiochem) diluted 1:50 in a blocking solution. Sections were washed several times with 0.02% TX-100 in PBS and the signal was detected by incubation for 90 min at room temperature with a secondary antibody conjugated to Cy3 (Jackson ImmunoResearch) diluted 1:250 in a blocking solution without TX-100. Hoechst nuclear staining was done by treating sections with Hoechst 33,342 dye (5 µg/ml in PBS; Invitrogen) for 15 min.

For double staining of hNuMA and TH, the same protocols as above were used. The mouse monoclonal anti-hNuMA antibody (Calbiochem) and polyclonal rabbit anti-TH antibody (Chemicon) diluted 1:50 and 1:500 in blocking solution were applied simultaneously. Visualization was performed by incubating sections for 90 min at room temperature with secondary antibodies conjugated to Cy3 and Cy2 (Jackson ImmunoResearch) diluted 1:250 in a blocking solution without TX-100. Following incubation in secondary antibodies Hoeschst nuclear staining was performed, as described above.

H. Nuclear Translocation of c-fos

The ability of cells to release dopamine in response to amphetamine was measured by induction of c-fos expression and nuclear translocation of the c-fos protein. For analysis of c-fos expression and translocation, rats were injected with dl-amphetamine 2 hours prior to sacrifice. Dl-amphetamine causes increased extracellular levels of DA from intact DA fibers. DA stimulates target striatal neurons resulting in the translocation of the immediate early response gene product c-fos to the nuclei of these neurons. Three weeks after transplantation, the rats were sacrificed by transcardial perfusion with fixative, and brain sections were stained for c-fos immunoreactivity.

Amphetamine induced-expression of c-fos in nuclei in the striatum was determined by immunocytochemistry. Frozen sections were washed three times in PBS, incubated for 15 min in 0.3% $H_2O_2$ in PBS, and blocked for 1 hr at room temperature in 3% NGS, 2% bovine serum albumin (BSA), 0.05% TX-100 in PBS. Sections were then incubated overnight at room temperature in polyclonal anti-c-fos antibody (Santa Cruz) diluted 1:1000 in 1% NGS, 1% BSA and 0.05% TX-100 in PBS. Sections were washed several times with 0.05% TX-100 in PBS, and then incubated for 2.5 hours with biotinylated goat anti-rabbit secondary antibody (Vector Laboratories) diluted 1:500 in 1% NGS and 1% BSA. This was followed by incubation in avidin-peroxidase conjugate (Vectastain ABC Elite, Vector Laboratories) in PBS for 2 hours. Visualization was conducted with DAB (20 mg/ml), 0.8% nickel sulfate, 0.005% $H_2O_2$ in 50 mM sodium acetate, 10 mM imidazole buffer (pH 7.0). Several washes with 0.05% TX-100 in PBS were performed between each step.

After staining cells for c-fos-immunoreactivity as described above, positive nuclei were counted using Neurolucida software (version 7.50.4, MicroBrightField Bioscience, Williston, Vt.). The sampling procedure was slightly different depending on the level being examined. At the level of the graft (0.48 mm from bregma), a grid was set with its center corresponding to the center of the graft under 2× magnification. Using the "contour" function, three contour plots were drawn; one on either side of the grid and one below. The area bound by the contours on either side was 0.25 mm² (area was 250 μm×1000 μm). The area bound by the contour below was half that value, i.e., 0.125 mm². Next, the magnification was increased to 20× and the NeuroLucida "meander scan" function was activated. The contours were then examined in 180× 180-μm increments for cells positive for c-fos using the computer cursor to mark cells as they were observed. A mirror point was established on the side contralateral to the graft using the center of the midline of the brain section as a reference. Once again, a grid was set with its center corresponding to this mirror point. Three contour plots were drawn at 2× magnification and cells positive for c-fos were marked under 20× magnification.

I. Additional Tests for Function of Dopaminergic Neurons (DA-Dependent Behaviors)

Additional tests for recovery and/or regeneration of dopaminergic neurons include amphetamine-induced rotation and forelimb paw placement.

Dopaminergic neurons are labeled by injection of fluorogold (a retrograde tracer) at the lesion/transplant site and the number of fluorogold-positive neurons is assayed after transplantation.

The phenotypes of transplanted cells and surrounding host cells are tested by staining for various markers, as follows. Neuronal markers: MAP2, beta III tubulin. Glial marker: glial fibrillary acidic protein (GFAP). Marrow adherent stromal cell marker: CD105.

J. Results

In all rats grafted with bone marrow-derived neural regenerating cells, dense tyrosine hydroxylase (TH) immunoreactive fibers (characteristic of dopaminergic neurons) were observed around the grafted sites, while only sparse or no tyrosine hydroxylase-immunoreactive fibers were observed at lesioned sites in control rats that had been injected with PBS.

Although a small number of grafted bone marrow-derived neural regenerating cells survived in the injection sites, as detected by expression of the human specific nuclear matrix protein, no tyrosine hydroxylase immunoreactivity was observed in soma of surviving grafted cells, suggesting that bone marrow-derived neural regenerating cells did not differentiate into dopaminergic neurons and that the tyrosine hydroxylase immunoreactive fibers observed around grafts were of host brain origin.

In sections co-stained for TH and human nuclear matrix protein, there was no clear overlap between hNuMA and TH staining, providing evidence for the host origin of the TH-positive fibers around the grafts. In addition, a positive correlation between the number of surviving cells and the density of TH-immunoreactive fibers near the grafts was observed. This effect was most noticeable in rats that received the higher dose cell grafts. In the first experiment, all three rats that received 21,000 cells/μl had more surviving cells and more dense TH-IR fibers than rats that received the low dose of cells. In the second experiment, 5 out of 6 rats that received 20,000 cells/μl had more surviving cells and 6 out of 6 had increased TH-IR fibers near the graft sites.

When expression and nuclear translocation of c-fos was assayed, two out of 6 rats displayed very high levels of c-fos positive nuclei around the graft sites. Hot spots of c-fos positive nuclei around the grafted neural regenerating cells in other rats were also observed. These observations suggest that the increase in TH-immunoreactive fibers is correlated with an increase in amphetamine-induced available DA near the NRC grafts in some rats, but not throughout the striatum and not in all grafts.

Taken together, these results indicate that transplantation of bone marrow-derived neural regenerating cells to sites of neural degeneration induce growth, survival and/or regeneration of host dopaminergic neurons toward the transplant, possibly by secretion of one or more trophic factors. Thus, transplantation of bone marrow-derived neural regenerating cells provides a technique for restoration of dopaminergic neurons in Parkinson's disease and other neurodegenerative conditions.

Example 7

Co-Culture with MASCs and NRCs Enhances Survival of, and Neurite Outgrowth from, Primary Neurons This example shows that primary cortical neurons grow well in complete neuronal medium but grow poorly, forming fewer and shorter neurites, in serum-free αMEM. However, when primary cortical neurons are cultured in a medium that does not support neuritogenesis (i.e., serum-free αMEM), and separated by a semipermeable membrane from either MASCs or NRCs, neurite outgrowth is enhanced. This suggests that both MASCs and NRCs produce soluble factors that support neuronal growth and neuritogenesis. The magnitude of the rescue effect appears similar for a given amount of MASCs or NRCs.

A. Preparation of Culture Plates

One day prior to an experiment, the lower compartments of Millicell 96-well cell culture insert plates (Millipore MACAC02S5, 0.4 μm pore size) were coated with a 10 μg/ml solution of poly-D-lysine (Sigma-Aldrich, St. Louis, Mo.) in water. Plates were incubated for one hour at room temperature, after which the lysine solution was aspirated, the plates dried for ten min, washed with PBS and filled with complete neuronal medium (Neurobasal™ medium supplemented with 2% B-27 and 0.5 mM GlutaMAX™). Treated plates, filled with neuronal medium, were stored at 4° C. until use.

B. Preparation of Donor Cells

Donor cells (MASCs and NRCs) were prepared and frozen as described in Examples 1-3. Cells to be tested (MASCs and NRCs from Donors D31 and D39) as well as MASCs from Donor D42 (used in this example as an internal standard) were thawed, plated in αMEM plus 10% FBS supplemented with penicillin and streptomycin (growth medium) in T225 flasks, at a density of 2×10⁶ cells/flask, for 5-7 days at 37° C./5% $CO_2$. For MASCs, the medium was also supplemented with 2 mM L-Glutamine. Cells were removed from the plates by replacing the medium with a small volume of 0.25% (w/v) trypsin, 1 mM EDTA, collected into a 50 ml tube, and growth medium was added (5-10 ml) to inactivate the trypsin. The tube was centrifuged at 200×g for 5 min, and the cell pellet was resuspended in 5-10 ml complete medium. A portion of the cell solution was counted in a hemacytometer (Hausser Scientific). Cell concentration was adjusted to $4 \times 10^5$/ml for the D42 standard donor cells, and to $2 \times 10^5$/ml for the cells to be tested (D31 and D39 MASCs and NRCs).

Millicell 96-well cell culture insert plate (Millipore MACAC02S5, 0.4 µm pore size) were prepared for cell plating by filling the inserts with 25 µl/well of growth medium. A portion of one of the cell suspension described in the preceding paragraph, sufficient to provide the desired number of donor cells, was added to each well; for example, to plate 20, 6.7, 2.2 and $0.75 \times 10^3$ cells/insert, 50, 17, 5.5 and 2 µl of cell suspension at $4 \times 10^5$/ml and 0, 33, 44.5, and 48 µl of growth medium, respectively, were added to a well. The insert portion was then lowered into a 96-well feeding compartment containing 250 µl/well of the same growth medium. Cells were cultured overnight at 37° C., 5% $CO_2$ and used the next day in the co-culture experiment.

C. Preparation of Rat Cortical Neurons

Rat cortex (E17) was obtained from BrainBits (Springfield, Ill.) in a medium provided by the supplier. For dissociation and preparation of cortical neurons, the medium was removed and replaced with 2 ml of a solution of 0.25% (w/v) trypsin, 1 mM EDTA (Gibco/Invitrogen, Carlsbad, Calif.). The mixture was incubated in a 37° C. water bath for 5-7 minutes. The trypsin solution was removed and the tissue was rinsed with 2 ml of αMEM supplemented with 10% fetal bovine serum (FBS). 2 ml of 0.25 mg/ml DNase I in Dulbecco's modified PBS was added to the trypsinized tissue and the suspension was mixed by vortexing for 30 sec. The suspension was mixed further by pipetting in and out of a 1 ml micropipette tip. Any large pieces of tissue remaining were discarded. The cell suspension was then placed in a 15 ml centrifuge tube and subjected to centrifugation at 200×g for 1 min. The supernatant was removed and the cells were resuspended in 2-3 ml of complete neuronal medium (Neurobasal™ medium supplemented with 2% B-27 and 0.5 mM GlutaMAX™). A portion of this neuronal cell suspension was dispensed into microcentrifuge tubes at a concentration of 40,000 cells/tube, the cells were pelleted, the medium was aspirated and the cell pellets were frozen at −20° C. These cells were used as standards in the LDH assay (see Section F below).

D. Co-Culture of Rat Primary Cortical Neurons with MASCs or NRCs

On the day of the experiment, polylysine-coated lower compartments, prepared as described in Section A above, were warmed in a 37° C. incubator for approximately 30 min. The neuronal medium was removed from the lower compartments and replaced with αMEM, except for several wells in which neuronal medium was retained, for use as positive controls.

Rat cortical neurons, prepared as in Section C above, were plated in the wells of the lower compartments at a density of 5,000 cells per well (96-well plates) and allowed to attach to the plate for one hour at 37° C.

Meanwhile, the donor cells described in Section B above were transferred into serum-free αMEM, by removing the medium from the wells above the membranes and replacing it with 75 µl of serum-free αMEM, then inserting the upper compartment into a lower compartment also containing serum-free αMEM and incubating for approximately 30 min at 37° C. Upper compartments, containing donor cells (MASCs and NRCs) in serum-free αMEM were then inserted into lower the compartments containing the primary cortical neurons in serum-free αMEM. Co-culture was conducted at 37° C., 5% $CO_2$ for 5-6 days. For the positive control, wells in the lower compartment contained neuronal medium rather than serum-free αMEM and no donor cells were present in the corresponding insert compartment.

E. Immunocytochemistry

Following co-culture, certain of the cultures were tested for neurite outgrowth by assaying for expression of MAP-2 (a neuronal marker). For this assay, cells in the lower wells were fixed in 4% paraformaldehyde (Electron Microscopy Sciences, Fort Washington, Pa.) for 20 min, then blocked with 0.3% Triton X-100, 5% normal donkey serum (Jackson Immunoresearch Laboratories, West Grove, Pa.) for one hour at room temperature. Antibody to MAP-2 (mouse monoclonal, Sigma-Aldrich, St Louis, Mo.) was added to the blocking solution and the incubation was continued for 1 hr at room temperature. After incubation for 1 hr, cells were washed with PBS and incubated with Cy3-conjugated AffiPure F(ab')$_2$ fragments of Donkey anti-Mouse IgG (minimal crossreaction, Jackson Immunoresearch Laboratories, West Grove, Pa.) diluted 1:1000, for one hour at room temperature. Cells were washed with PBS, the wells were then filled with PBS and staining was assayed on Axiovert 40CFL (Zeiss, Germany); photographs were taken using an Axio-Cam MRm.

Figure 1:
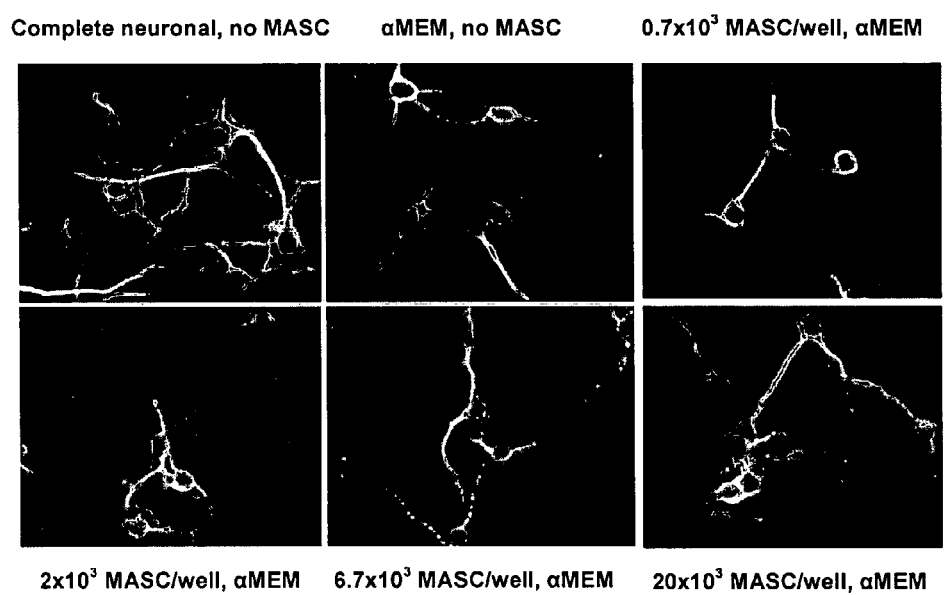
FIG. 1 shows effects of factors, secreted by MASCs, on growth of neurites in cultures of primary rat neurons, as assessed by MAP2 staining. Neurons were cultured in complete neurobasal medium (positive control; upper left panel) or in αMEM (negative control; upper center panel) or were co-cultured for two days in αMEM, with different numbers of MASC (as indicated in the Figure) separated from rat neurons by a semipermeable membrane (upper right and three lower panels.

FIG. 1 shows effect of co-culture with MASCs on neurite outgrowth in primary rat cortical neurons, assayed by immunocytochemistry for MAP-2, as described in the preceding paragraph. MAP-2 labeling revealed extensive neurite outgrowth when neurons were cultured in complete neuronal medium (top left panel of FIG. 1), and fewer, shorter neurites when neurons were cultured in serum-free αMEM (top center panel of FIG. 1). When neurons were co-cultured with MASCs in αMEM, the number of processes was positively correlated with the number of MASCs that were co-cultured with the neurons (FIG. 1, top right and bottom panels). Similar supportive effects on neurite outgrowth from primary cortical neurons were observed in co-cultures with NRCs.

F. LDH Assay for Cell Survival

Survival of certain of the samples of neurons, co-cultured with MASCs and NRCs in serum-free αMEM, was assessed by determining levels of intracellular lactate dehydrogenase (LDH). For these samples, inserts containing donor cells were removed and medium was aspirated from the lower compartments, which were then washed once with PBS. Cells attached to the plate were then lysed by adding 0.15 ml of 2% (v/v) Triton X-100 to each well. 0.1 ml of the Triton lysate was removed from each well and transferred to a fresh well for LDH assay using a Roche LDH assay kit. A standard curve was prepared using serial dilutions of the frozen cells obtained as described in Section C above, lysed in 500 µl of 2% Triton X-100.

For the LDH assay, 100 µl of a mixture of reagents A and B from the LDH kit, prepared according to the manufacturer's protocol, was added to each well. Approximately 20-30 min later, color was measured on a SpectraMax Plus (Molecular Devices) at a wavelength of 490 nm and a reference wavelength 650 nm. Typically, color was allowed to develop until the standard containing the highest cell concentration provided a reading of approximately 1 OD unit. Measurements were analyzed using Soft Max Pro Software and a standard curve was constructed using quadratic fit.

Figure 2:
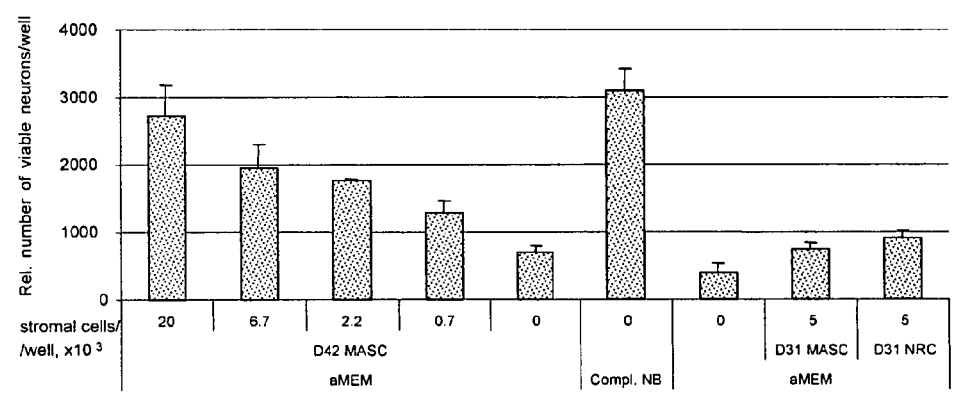
FIG. 2 shows relative numbers of surviving neurons, based on assay of intracellular LDH, in primary rat cortical neurons that had been co-cultured with MASCs and NRCs. The leftmost five bars show results from a titration of MASCs from Donor 42 (D42), co-cultured with cortical neurons in serum-free αMEM. Numbers of D42 MASCs (×10) placed into co-culture with the neurons are shown along the abscissa. The sixth bar from the left show intracellular LDH from positive control neurons that had been grown in complete neuronal medium ("Compl. NB") without co-culture.

FIGS. 2 and 3 show results of 2 independent experiments in which assay for intracellular LDH was used to measure relative numbers of surviving neurons after co-culture in serum-free αMEM with MASCs and NRCs from two different donors. In both experiments, D42 MASCs were also used as an internal standard. D42 MASC cells were titrated in each experiment to ensure the ability of the assay to detect differences in levels of neuronal survival.

In the experiment shown in FIG. 2, equal numbers of MASCs and NRCs from Donor 31 ($5 \times 10^3$/well) produced similar effect on neuronal survival (FIG. 2, rightmost two bars). The effect was lower than that obtained from the same number of D42 MASCs, as can be seen from titration curve of D42 MASC shown in the left-most five bars in FIG. 2.

In the experiment shown in FIG. 3, MASCs and NRCs from Donor 39 (D39) were tested at 2 different concentrations ($10 \times 10^3$/well and $5 \times 10^3$/well). Again, MASCs and NRCs provided similar level of rescue activity (FIG. 3, rightmost four bars). In this experiment, however, D39 MASC and NRCs were more active than the D42 MASCs used as standards, as can be seen from the titration curve of D42 MASCs (left-most five bars of FIG. 3).

Example 8

Rescue of Damaged Neural Cells Following Co-Culture with Bone Marrow Stromal Cells or Neural Regenerating Cells To provide an in vitro model of neural injury, primary cortical neurons were subjected to oxygen/glucose deprivation (OGD), which results in significant cell damage within 24 hours. Immediately following OGD, neurons were co-cultured with either human marrow adherent stromal cells or human neural regenerating cells, both of which were prepared as described in Examples 1 and 2. These donor cells were separated from the oxygen/glucose-deprived neurons by a 0.4 μm pore size membrane, which allows the passage of molecules but excludes cell-cell contact. In both cases, the presence of the donor cells rescued neural cells following OGD, as described below.

Cortical neurons from E17 Sprague-Dawley rats were plated in poly-d-lysine-coated 12-well plates at 6,000 cells/cm$^2$ and cultured in Neurobasal™ medium supplemented with 2% B-27 and 0.5 mM GlutaMAX™ (Neuronal medium) at 37° C./5% $CO_2$. After maturing for 14 days in vitro, neurons were subjected to OGD (0% oxygen and culture in Dulbecco's-modified Eagle's medium without glucose) for 60 minutes. Control cultures were held at atmospheric oxygen (normoxia) in neuronal medium for the same time. Immediately afterwards, the medium was changed again to neuronal medium and an insert containing neural regenerating cells, marrow adherent stromal cells, or medium only was placed in the well. Neuronal medium was used for all groups (n=6 matched donors per cell type; i.e., MASCs were obtained from six different donors and a portion of each donor culture was used for production of NRCs). Two to four wells of cells per group were used for the experiment.

The base of the insert was a polyethylene terephthalate (PET) membrane with a pore size of 0.4 μm, which allows the exchange of molecules but prevents cell-cell contact. Marrow adherent stromal cells or neural regenerating cells were plated on the insert in the appropriate growth medium, which was rinsed and changed to neuronal medium prior to being placed into the wells with neurons. Donor cells were 80-100% confluent on the insert (0.9 cm$^2$) at the time they were added to the wells containing neurons. At 24 hours post-OGD, cell damage/death was assessed by quantifying lactate dehydrogenase (LDH) release from the cultured neurons (i.e., extracellular LDH), and normalizing to the appropriate control conditions. Neurons in control conditions (non-OGD) also received inserts containing neural regenerating cells, marrow adherent stromal cells, or media only, to account for LDH release from the donor cells, since LDH is able to pass through the membrane separating the donor cells from the neurons. Results were thus reported as the fold increase in LDH release for neurons that underwent OGD and were then co-cultured with an insert of either type of donor cell or with medium only, compared to neurons under control (non-OGD) condition that were co-cultured with an insert containing the same donor cell type or medium. LDH was assayed using the "Cytotoxicity Detection Kit (LDH)" from Roche Applied Science (Indianapolis, Ind.). See Example 7 for details of the LDH assay, noting that in the present example, extracellular LDH was assayed as a measure of cell death; while, in Example 7, cells were separated from the medium and lysed for the measurement of intracellular LDH.

The results, shown in FIG. 4, indicate that exposing the damaged neurons to marrow adherent stromal cells or neural regenerating cells significantly reduces cell damage/death following OGD (measured as extracellular LDH), compared to exposing neurons to medium only ($p<0.05$). Moreover, because the donor cells were not in direct contact with the injured neurons, the observed reduction in cell death is consistent with the secretion of one or more trophic factors by the donor cells.

Example 9

Rescue of Damaged Neural Cells Following Co-Culture with Conditioned Medium from Bone Marrow Stromal Cells or Neural Regenerating Cells To provide further evidence that trophic factors secreted by marrow adherent stromal cells or neural regenerating cells rescue neurons subjected to an ischemic insult, neurons injured by OGD were cultured with conditioned medium from marrow adherent stromal cells or from neural regenerating cells. To prepare conditioned medium, donor cells (n=5 matched donors per cell type, 2-4 wells per group) were cultured for 24 hours in one of the following media: 1) fresh neuronal medium (composition described supra), 2) neuronal medium in which OGD injured neurons had been cultured for 24 hours, or 3) neuronal medium in which control neurons had been cultured for 24 hours. Conditioned medium was then collected from the donor cell cultures and added to cultured neurons that had undergone OGD or to control neurons that had not undergone OGD. LDH release was assayed 24 hours later.

The results are shown in FIG. 5. In all cases, injured neurons exposed to conditioned medium exhibited significantly reduced cell damage (measured by LDH release compared to control cells that had not undergone OGD) at 24 hours following OGD ($p<0.05$). There were no differences observed between the three types of donor cell-conditioned media, which indicates that any substances released by injured neurons, over the 24-hour period of co-culture with the donor cells, did not significantly affect the ability of the donor cell-conditioned medium to rescue injured neurons. In addition, there was no significant difference in the rescue effect of media conditioned by either marrow adherent stromal cells or neural regenerating cells.

To determine whether this rescue effect has a dose response, conditioned medium was obtained by culturing donor cells (n=5 matched donors per cell type, 2-4 wells per group) in neuronal medium for 24 hours. This conditioned medium was added either to neurons that had been subjected to OGD or to control neurons at dilutions of 1:1, 1:10, 1:25, 1:50, 1:100 or 1:200 and neurons were cultured in the conditioned medium for 24 hours. The results, shown in FIG. 6, indicate that rescue of injured neurons by conditioned medium (from both marrow adherent stromal cells and neural regenerating cells) is dose-dependent.

Example 10

Rescue of Damaged Neural Cells Following Co-Culture with Neural Regenerating Cells that Had been Pre-Cultured with Damaged Neural Cells To determine if the injured neural environment influences the ability of the donor cells to rescue injured neurons, marrow adherent stromal cells (n=1 donor) or neural regenerating cells (n=3 donors) were plated on a PET insert (see Example 7) and pre-cultured for 24 hours either with neurons that had been injured by OGD 24 hours previously or with control uninjured neurons. Following this pre-culture, the marrow adherent stromal cell-containing or neural regenerating cell-containing inserts were placed into wells containing either neurons that had undergone OGD immediately prior to the addition of the inserts or control, uninjured neurons. After a further 24 hours, LDH release was assayed (2-4 wells per group).

The results of this experiment indicated that both marrow adherent stromal cells and neural regenerating cells, pre-cultured with either injured or uninjured neurons, were able to rescue OGD-damaged neurons. Both MASCs and NRCs had roughly equivalent rescue activities, and pre-culture with either control or OGD-damaged neurons did not affect the rescue activities of either MASCS or NRCs. (This may be due to the fact that conditioned media were used undiluted in this experiment, and the rescue effect exceeded the differential range of the assay.) These results indicate that the donor cells may respond to cues from injured neural cells that affect the production and/or secretion of one or more diffusible trophic factors.

Example 11

Preparation of Primary Hippocampal Slices

Rat organotypic hippocampal slices (OHS) were obtained from the brains of 9 day old Sprague-Dawley rat pups according to the following procedure:

1) A female rat with pups (P9) was delivered from Charles River Laboratories (Wilmington, Mass.). Until the time of sacrifice, animals were housed in a sealed cardboard box provided by Charles River that contains sufficient food and water. Animals were kept for less than 5 hours prior to processing.

2) Pups were processed for dissection one at a time. A single pup was placed in an air-tight container with dry ice (for $CO_2$ production).

3) The anesthetized pup was removed from the container, and quickly submerged in 70% ethanol in a glass beaker, then rapidly decapitated with scissors. All skin was removed from the skull.

4) The carcass was transferred to a bio-safety cabinet. The brain was removed from the skull and placed into ice-cold buffer (e.g., PBS).

5) The hippocampal formation was dissected out of the brain with curved forceps and placed onto a tissue chopper stage (McIlwain), where it was cut into 400 µm slices.

6) Slices were placed on single-well membrane inserts (Millipore, see Examples 7 and 8), which were in turn placed inside cell culture plates containing 50% Hank's modified Eagle's medium, 25% Hank's balanced salt solution, 25% horse serum, and 1% penicillin/streptomycin; supplemented with 8.5 mM HEPES, 5.5 mM glucose, and 0.5 mM GlutaMAX™.

7) Plates containing OHS were then stored in a $CO_2$ incubator at 35° C.

8) OHS were used for experiments after 4-6 days in culture.

Example 12

Rescue of Damaged Hippocampal Slices Following Co-Culture with Bone Marrow Stromal Cells or Neural Regenerating Cells To study trophic support of damaged neurons by marrow adherent stromal cells and neural regenerating cells using an in vivo model, hippocampal brain slices were employed. The hippocampus was chosen because of the well-defined neuronal pathways contained within this structure and the fact that there is ample literature on the culture of organotypic hippocampal slices.

Hippocampal slices (P9 rats, 400 µm at dissection) were cultured on an insert (Millipore), the base of which was a polyethylene terephthalate (PET) membrane with a pore size of 0.4 µm, which allows the exchange of molecules but prevents cell-cell contact. The insert was placed into a well containing 50% Hank's modified Eagle's medium, 25% Hank's balanced salt solution, 25% horse serum, and 1% penicillin/streptomycin; supplemented with 8.5 mM HEPES, 5.5 mM glucose, and 0.5 mM GlutaMAX™. After 1 day, the medium was slowly changed over to Neurobasal™ medium supplemented with 2% B-27 and 1.0 mM GlutaMAX™, ("slice medium"). After 4-6 days in culture, slices were subjected to OGD (0% oxygen and DMEM without glucose) for 90 minutes. Control cultures received slice medium and were held at atmospheric oxygen (normoxia) for the same amount of time. Immediately following OGD, the inserts (n=6 matched donors per cell type, 4-6 inserts per group) were moved to wells containing (1) marrow adherent stromal cells (at 70-100% confluence) in slice medium, (2) neural regenerating cells (at 70-100% confluence) in slice medium or (3) slice medium only. LDH release was quantified 24 and 48 hours later.

The results, shown in FIG. 7, indicate that slices cultured in the presence of donor cells (i.e., marrow adherent stromal cells or neural regenerating cells) for 24 and 48 hours following OGD undergo significantly less cell damage than those cultured in slice medium alone ($p<0.05$).

Cells within the slices are also analyzed by propidium iodide uptake to assess which cells within the slice are damaged.

Example 13

Rescue of Damaged Hippocampal Slices Following Transplantation of Bone Marrow Stromal Cells or Neural Regenerating Cells Donor cells (i.e., marrow adherent stromal cells or neural regenerating cells) are injected directly into hippocampal slices to examine how donor cells influence host tissue when direct cell to cell contact is involved and also to study the effect of the injury environment on the donor cells.

To facilitate visualization of the donor cells, they were infected with a lentivirus comprising sequences encoding green fluorescent protein (GFP) under the transcriptional control of a CMV promoter. Following infection at a multiplicity of infection (MOI) of 3 viral particles per cell, approximately 50-60% of the donor cells (either neural regenerating or marrow adherent stromal cells; n=1 matched donor per cell type) were fluorescent, and stable fluorescence was observed for at least 1 month in culture.

These GFP-positive donor cells were delivered to hippocampal slices by pipetting 0.5 µl of cells (at a concentration of ~1,000 cells/µl) onto the surface of the slice. The behavior of the GFP-positive donor cells within the thick (200-400 µm) slices is compared with respect to survival, proliferation, migration and integration into the tissue following transplantation into normal or injured (e.g., ischemic) brain slices and monitored using confocal microscopy. For example, the slices are monitored by confocal microscopy at various time periods (e.g., 2 hours) after delivery of donor cells to determine donor cell number, location (with respect to both anatomy and in the z-dimension), and morphology. This analysis is repeated at, for example, 2 and 5 days post-injection and compared to baseline levels to assess survival/proliferation, migration, and integration. Propidium iodide incorporation is also used to assess both host and donor cell viability. Subsequent analysis involves fixing the tissue slices and staining for markers of proliferation, cell death and phenotype.

Comparison of the location of the transplanted cells and the location of regenerating or recovering host neural cells provides information on the extent of the trophic effect mediated by the transplanted cells. The number and location of the transplanted cells is also analyzed to determine the extent of cell division and translocation of the transplanted cells. Morphology of the transplanted cells and surrounding host cells is assessed, and the differentiated state of the transplanted cells and surrounding host cells is analyzed by cytochemical and immunological techniques.

Example 14

Rescue of Damaged Hippocampal Slices Following Co-Culture with Conditioned Medium from Bone Marrow Stromal Cells or Neural Regenerating Cells The extent to which donor cell-conditioned medium affects injured hippocampal tissue slices was also examined. For this study, conditioned medium was prepared by adding fresh slice medium to plated donor cells (n=5 matched donors per cell type, 5-6 wells per group). After 24 hours in culture, donor cell-conditioned medium was collected and added either to wells containing inserts with hippocampal slices that had undergone OGD or to wells containing control slices that had not undergone OGD. LDH release was assayed 24 hours later. FIG. 8 shows that the donor cell-conditioned medium significantly improved the viability of the injured slices ($p<0.05$), with no significant difference in the rescue effect of media conditioned by marrow adherent stromal cells or neural regenerating cells.

Example 15

Rescue of Damaged Neurons Following Co-Culture with Conditioned Medium from Neural Regenerating Cells that Had been Pre-Cultured with Damaged Hippocampal Slices To determine if the injured neural environment influences the ability of the donor cells to rescue injured neurons, neural regenerating cells (n=3 donors) were plated in 6 well plates and co-cultured for 48 hours either with hippocampal slices that had been injured by OGD or with control uninjured slices (see Example 12). Following this pre-culture, medium was removed, and the two types of neural regenerating cell-conditioned medium were diluted 1:25 in neuronal medium and placed into wells containing neurons that had undergone OGD immediately prior to the addition of the conditioned medium (see Example 8). After a further 24 hours, LDH release was assayed (4 wells per group).

FIG. 9 shows the results of this experiment. Injured neurons that were cultured with conditioned medium from neural regenerating cells co-cultured with injured brain slices had significantly less cell damage compared to those that were cultured with conditioned medium from neural regenerating cells co-cultured with control, uninjured slices ($p<0.05$). This result provides further evidence that the donor cells respond to cues from injured neural cells that affect the production and/or secretion of one or more diffusible trophic factors from the donor cells.

Example 16

Trophic Factor Secretion by Bone Marrow Stromal Cells and Neural Regenerating Cells The data presented above provide evidence that bone marrow stromal cells and stromal cell-derived neural regenerating cells are able to rescue injured neural cells by provision of one or more trophic factors. To begin to identify the critical trophic factors involved, the protein levels of specific candidate trophic factors in donor cell-conditioned medium were quantified. Bone marrow stromal cells and neural regenerating cells (n=5 matched donors per cell type) were cultured in αMEM supplemented with 10% fetal bovine serum and 1% penicillin-streptomycin to a density of ~15,000 cells/cm². The medium was then replaced with Opti-MEM® medium (~200,000 cells per ml), and the conditioned medium was collected 72 hours later. The amounts of the following ten cytokines were quantified using a Quantibody™ Custom Array (RayBiotech, Inc.): bone morphogenetic protein-7 (BMP-7), brain derived neurotrophic factor (BDNF), basic fibroblast growth factor (bFGF), glial cell line-derived neurotrophic factor (GDNF), hepatocyte growth factor (HGF), heparin binding-epidermal growth factor like growth factor (HB-EGF), nerve growth factor (b-NGF), platelet derived growth factor (PDGF-BB), insulin-like growth factor-I (IGF-I), and vascular endothelial growth factor (VEG-F). Results are shown in Table 1. Both hepatocyte growth factor and vascular endothelial growth factors were found in significant amounts (i.e. within the range of the standards tested), and there was not a significant difference between concentrations present in bone marrow stem cell- or neural regenerating cell-conditioned media.

TABLE 1

| Cytokine | Standards Range (pg/ml) | Avg MASCs (n = 5) (pg/ml) | Avg NRCs (n = 5) (pg/ml) |
|---|---|---|---|
| BDNF | 25-2,000 | 4.4 | 25.1 |
| bFGF | 49-4,000 | 0.0 | 0.0 |
| BMP-7 | 494-40,000 | 0.0 | 59.3 |
| b-NGF | 99-8,000 | 1.4 | 10.1 |

TABLE 1-continued

| Cytokine | Standards Range (pg/ml) | Avg MASCs (n = 5) (pg/ml) | Avg NRCs (n = 5) (pg/ml) |
|---|---|---|---|
| GDNF | 49-4,000 | 0.0 | 0.0 |
| HB-EGF | 49-4,000 | 0.0 | 0.0 |
| HGF | 49-4,000 | 67.8 | 72.5 |
| IGF-I | 123-10,000 | 0.0 | 0.0 |
| PDGF-BB | 12-1,000 | 0.0 | 0.0 |
| VEGF | 49-4,000 | 2519.7 | 2858.2 |

"0.0" = below 0.1-0.5 of the lowest standard concentration

Example 17

Further Analysis of Trophic Factor Secretion by Bone Marrow Stromal Cells and Neural Regenerating Cells Bone marrow stromal cells and neural regenerating cells (n=5 matched donors per cell type) were cultured in αMEM supplemented with 10% fetal bovine serum and 1% penicillin-streptomycin to a density of ~15,000 cells/cm$^2$. The medium was then replaced with Opti-MEM® reduced serum medium (~200,000 cells per ml), and the conditioned medium was collected 72 hours later. A semi-quantitative custom array (Quantibody® Array, RayBiotech, Inc., Norcross, Ga.) was used to determine which of 30 selected cytokines were detectable in the donor cell-conditioned medium and to compare relative amounts of cytokine levels among different samples. Arrays were exposed to conditioned medium from MASCs and from NRCs obtained as described previously in this paragraph.

Results are summarized in Table 2. The first column identifies the factor whose presence was assayed. The second column shows the number of MASC conditioned medium preparations (out of a total of five) that showed levels of the particular factor that were 1.5-fold greater than the levels of that factor in Opti-MEM®. The third and fourth columns show the average level of a given factor among the five samples, presented as the fold change in the normalized signal intensity compared to that of an array exposed to Opti-MEM® only (third column), with standard deviation (fourth column). A fold change of 1.5 or greater, compared to Opti-MEM® only, indicates that the cytokine detected in the conditioned medium was due to the presence of the donor cells.

The fifth column shows the number of NRC conditioned medium preparations (out of a total of five) that showed levels of the particular factor that were 1.5-fold greater than the levels of that factor in Opti-MEM®. The sixth and seventh columns show the average level of a given factor among the five samples, presented as the fold change in the normalized signal intensity compared to that of an array exposed to Opti-MEM® only (sixth column), with standard deviation (seventh column). A fold change of 1.5 or greater, compared to Opti-MEM® only, indicates that the cytokine detected in the conditioned medium was due to the presence of the donor cells.

The eighth column shows the number of donors (out of a total of five) in which the amount of a particular factor was greater in NRC-conditioned medium that it was in MASC-conditioned medium. The ninth and tenth columns show, for each factor tested, the ratio of its level in NRC-conditioned medium to its level in MASC-conditioned medium and standard deviation, respectively.

The results indicate that the following 10 cytokines were found in donor cell conditioned medium from either MASCs or NRCs: bone morphogenetic protein-4 (BMP-4), Dickkopf-1 (Dkk-1), fibroblast growth factor-7 (FGF-7), heparin binding-epidermal growth factor like growth factor (HB-EGF), interleukin-6 (IL-6), interleukin-8 (IL-8), monocyte chemoattractant protein-1 (MCP-1), matrix metalloproteinase-1 (MMP-1), platelet derived growth factor (PDGF-AA), and vascular endothelial growth factor (VEGF). Four of these were consistently found at increased levels in neural regenerating cell-conditioned medium compared to bone marrow stromal cell-conditioned medium: DKK-1, IL-6, IL-8, and MCP-1.

TABLE 2

| | # donors MSC-CM > 1.5× OptiMEM | MSC (n = 5) | | # donors NRC-CM > 1.5× OptiMEM | NRC (n = 5) | | # donors NRC > MSC | NRC/MSC | |
|---|---|---|---|---|---|---|---|---|---|
| | | AVG | SD | | AVG | SD | | AVG | SD |
| BDNF | 0 | 0.58 | 0.25 | 0 | 0.80 | 0.29 | — | 1.5 | 0.7 |
| bFGF | 0 | 0.99 | 0.23 | 1 | 1.16 | 0.28 | — | 1.2 | 0.4 |
| BMP-4 | 2 | 1.65 | 0.85 | 4 | 2.23 | 0.81 | 4 | 1.6 | 0.8 |
| BMP-6 | 0 | 0.64 | 0.23 | 0 | 0.69 | 0.21 | — | 1.2 | 0.6 |
| BMP-7 | 1 | 1.14 | 0.49 | 2 | 1.45 | 0.54 | — | 1.4 | 0.9 |
| b-NGF | 0 | 0.91 | 0.33 | 1 | 1.26 | 0.29 | — | 1.5 | 0.3 |
| CNTF | 0 | 0.80 | 0.22 | 0 | 0.83 | 0.19 | — | 1.1 | 0.2 |
| Dkk-1 | 4 | 2.66 | 1.11 | 5 | 12.47 | 0.48 | 5 | 5.8 | 3.4 |
| Dkk-4 | 0 | 0.53 | 0.19 | 0 | 0.68 | 0.21 | — | 1.6 | 1.2 |
| EGF | 0 | 0.61 | 0.16 | 0 | 0.85 | 0.30 | — | 1.4 | 0.3 |
| Erythropoietin R | 0 | 0.82 | 0.29 | 0 | 1.05 | 0.22 | — | 1.4 | 0.4 |
| FGF-7 | 5 | 3.71 | 1.44 | 4 | 2.22 | 0.60 | 1 | 0.7 | 0.4 |
| GCSF | 0 | 0.65 | 0.18 | 0 | 0.89 | 0.31 | — | 1.4 | 0.3 |
| GDNF | 0 | 0.81 | 0.25 | 0 | 0.90 | 0.14 | — | 1.3 | 0.7 |
| HB-EGF | 2 | 2.27 | 2.19 | 2 | 1.99 | 1.89 | 2 | 1.0 | 0.6 |
| HGF | 0 | 0.93 | 0.28 | 0 | 0.97 | 0.37 | — | 1.0 | 0.2 |

TABLE 2-continued

| | | | | | | | | | |
|---|---|---|---|---|---|---|---|---|---|
| IGF-I | 0 | 0.84 | 0.21 | 0 | 0.96 | 0.22 | — | 1.2 | 0.2 |
| IL-1 alpha | 0 | 0.68 | 0.21 | 0 | 0.79 | 0.23 | — | 1.2 | 0.4 |
| IL-6 | 5 | 5.02 | 2.41 | 5 | 20.73 | 24.00 | 5 | 3.8 | 2.7 |
| IL-8 | 0 | 0.77 | 0.05 | 5 | 2.84 | 1.36 | 5 | 3.7 | 1.7 |
| LIF | 0 | 0.75 | 0.16 | 0 | 0.95 | 0.31 | — | 1.3 | 0.2 |
| MCP-1 | 5 | 17.02 | 13.13 | 5 | 50.30 | 20.29 | 5 | 4.7 | 4.6 |
| MMP-1 | 0 | 0.87 | 0.15 | 3 | 1.92 | 1.54 | 4 | 2.3 | 2.0 |
| NT-3 | 0 | 0.78 | 0.23 | 0 | 1.05 | 0.29 | — | 1.4 | 0.4 |
| PDGF-AA | 5 | 2.71 | 1.01 | 5 | 3.47 | 0.52 | 4 | 1.4 | 0.2 |
| SDF-1 | 0 | 0.66 | 0.41 | 0 | 0.72 | 0.43 | — | 1.2 | 0.4 |
| TGF-alpha | 0 | 0.93 | 0.26 | 1 | 1.16 | 0.29 | — | 1.3 | 0.2 |
| TGF-beta | 0 | 0.98 | 0.28 | 0 | 1.16 | 0.29 | — | 1.2 | 0.4 |
| TNF-alpha | 0 | 0.81 | 0.19 | 0 | 1.01 | 0.23 | — | 1.3 | 0.2 |
| VEGF | 5 | 35.01 | 19.64 | 5 | 45.18 | 8.86 | 4 | 1.8 | 1.5 | bold: more than 1.5× greater than OptiMEM® only indicating detection of the cytokine in conditioned media is due to presence of donor cells Example 18

Trophic Factor Secretion in the Presence of Heparin

Certain growth factors are known to contain heparin binding domains and therefore, although secreted by donor cells, may not become soluble in the medium because they instead bind to the endogenous heparin on the cell. To test for the production of such factors by MASCs and/or NRCs, heparin (50 µg/ml) was added to the cultures after the cells were transferred into Opti-MEM® and once daily thereafter until conditioned medium was collected (a total of three days). If such heparin-binding growth factors are produced and secreted by donor cells, the exogenous heparin in the medium will compete for their binding and increase the chances of their being collected in the conditioned medium. Conditioned medium was assayed as described in Example 17.

Results are shown in Table 3. The first column identifies the factor whose presence was assayed. The second column show the level of a given factor in conditioned medium from a single sample of MASCs. The third column shows the level of the factor in a sample of MASCs from the same donor (D46) in which heparin was present during generation of the conditioned medium. The fourth column show the level of a given factor in conditioned medium from a single sample of NRCs, obtained from the same donor as the MASCs characterized on columns 2 and 3. The fifth column shows the level of the factor in a sample of NRCs from the same donor (D46) in which heparin was present during generation of the conditioned medium. The sixth column show the level of a given factor in conditioned medium from a single sample of NRCs, obtained from a different donor (D47). The seventh column shows the level of the factor in a sample of NRCs from donor D47 in which heparin was present during generation of the conditioned medium. The eighth column shows the fold increase in levels of the factor in heparin-containing cultures, averaged across all three samples (D46 MASC, D46 NRC, and D47 NRC).

The results showed that addition of heparin to the culture medium increased levels, in the conditioned medium, of three factors secreted in the absence of heparin (DKK-1, IL-6, and VEGF). In addition, increased levels of hepatocyte growth factor (HGF), which was not detected in the absence of heparin (see Example 16), was also observed in the donor cell-conditioned media. Finally, in one donor, increased levels of transforming growth factor alpha (TGF-α, also not detected in the absence of heparin) was also observed. These results point to the existence of heparin-binding factors secreted by the donor MASCs and NRCs.

TABLE 3

| | D46 MSC | D46 MSC + heparin | D46 NRC | D46 NRC + heparin | D47 NRC | D47 NRC + heparin | AVG Fold Increase |
|---|---|---|---|---|---|---|---|
| DKK-1 | 2.17 | 18.89 | 12.74 | 60.69 | 12.31 | 49.98 | 5.8 |
| HGF | 1.21 | 11.79 | 1.38 | 11.51 | 0.66 | 2.45 | 7.3 |
| IL-6 | 4.27 | 5.99 | 7.47 | 13.66 | 8.64 | 20.93 | 1.9 |
| TGF-alpha | 0.68 | 1.25 | 0.96 | 2.40 | 0.95 | 1.48 | 2.0 |
| VEGF | 62.27 | 92.90 | 50.31 | 81.63 | 31.14 | 81.23 | 1.9 |

Example 19

Quantitation of Trophic Factors Secreted by MASCs and NRCs

Conditioned medium was collected from MASCs and NRCs (n=8 matched donors per cell type) as described in Examples 16 and 17, and the concentrations, in the conditioned medium, of ten of the factors identified in Examples 16-18 were determined using a Quantibody™ custom array (Ray Biotech, Inc.). The results, shown in Table 4, confirm the previous findings. With the exception of BMP-4 and HB-EGF, all the cytokines tested were found to be present (within the range of standards used in the assay) in medium conditioned by bone marrow stromal cells and/or neural regenerating cells. Also confirming the results provided in Example 17, four of these proteins (DKK-1, IL-6, IL-8, and MCP-1) were consistently found at increased levels in neural regenerating cell-conditioned medium compared to bone marrow stromal cell-conditioned medium. The inability to detect BMP-4 in both cell types, and the inability to detect HB-EGF in NRCs may be due to their levels being outside of the range of standards for this particular array.

TABLE 4

| Cytokine | Standards Range (pg/ml) | Avg MASCs (n = 8) (pg/ml) | Avg NRCs (n = 8) (pg/ml) |
|---|---|---|---|
| BMP-4 | 1,200-10,000 | 0.0 | 0.0 |
| Dkk-1 | 1,200-10,000 | 7648.0 | 46931.3 |
| FGF-7 | 247-20,000 | 459.8 | 349.1 |
| HB-EGF | 123-10,000 | 10.7 | 0.0 |
| HGF | 49-4,000 | 251.2 | 263.5 |
| IL-6 | 25-2,000 | 1651.6 | 4802.3 |
| IL-8 | 12-1,000 | 0.0 | 417.0 |
| MCP-1 | 25-2,000 | 936.9 | 2098.2 |

TABLE 4-continued

| Cytokine | Standards Range (pg/ml) | Avg MASCs (n = 8) (pg/ml) | Avg NRCs (n = 8) (pg/ml) |
|---|---|---|---|
| PDGF-AA | 247-20,000 | 98.5 | 154.1 |
| VEGF | 123-10,000 | 10949.0 | 11593.4 |

'0.0' = below 0.1-0.5 of the lowest standard concentration

What is claimed is:

1. A method for promoting survival of neural cells in a host by provision of one or more trophic factors, wherein the method comprises transplanting bone marrow-derived neural regenerating cells at or near a site of neural degeneration in the host, wherein the neural regenerating cells are obtained by a process comprising the steps of:
   (a) providing a culture of marrow adherent stromal cells;
   (b) contacting the cell culture of step (a) with a polynucleotide comprising sequences encoding a Notch intracellular domain (NICD), wherein the NICD consists of amino acids 1703-2504 of the Notch-1 protein;
   (c) selecting cells that comprise the polynucleotide of step (b); and
   (d) further culturing the selected cells of step (c) in the absence of selection;
   and further wherein the neural regenerating cells provide trophic factors that promote survival of the neural cells in the host.

2. The method of claim 1, wherein said neural cells are neurons.

3. The method of claim 1, wherein the site of neural degeneration is in the central nervous system.

4. The method of claim 3, wherein the site of neural degeneration is caused by Parkinson's Disease.

5. The method of claim 1, wherein the site of neural degeneration is in the peripheral nervous system.

6. The method of claim 1, wherein the one or more trophic factors are selected from the group consisting of vascular endothelial growth factor, hepatocyte growth factor, bone morphogenetic protein 4, Dkk-1, fibroblast growth factor-7, heparin-binding epidermal growth factor-like growth factor, interleukin-6, interleukin-8, monocyte chemoattractant protein-1, matrix metalloproteinase-1, platelet-derived growth factor AA and transforming growth factor alpha.

7. A method for stimulating growth of neural cells in a host by provision of one or more trophic factors, wherein the method comprises transplanting bone marrow-derived neural regenerating cells at or near a site of neural degeneration in the host, wherein the neural regenerating cells are obtained by a process comprising the steps of:
   (a) providing a culture of marrow adherent stromal cells;
   (b) contacting the cell culture of step (a) with a polynucleotide comprising sequences encoding a Notch intracellular domain (NICD), wherein the NICD consists of amino acids 1703-2504 of the Notch-1 protein;
   (c) selecting cells that comprise the polynucleotide of step (b); and
   (d) further culturing the selected cells of step (c) in the absence of selection;
   and further wherein the neural regenerating cells provide trophic factors that stimulate growth of the neural cells in the host.

8. The method of claim 7, wherein outgrowth of nerve fibers is stimulated.

9. The method of claim 8, wherein the nerve fibers are axons.

10. The method of claim 8, wherein the nerve fibers are dendrites.

11. The method of claim 7, wherein new synapses are formed.

12. The method of claim 7, wherein the site of neural degeneration is in the central nervous system.

13. The method of claim 12, wherein the site of neural degeneration is caused by Parkinson's Disease.

14. The method of claim 7, wherein the site of neural degeneration is in the peripheral nervous system.

15. The method of claim 7, wherein the one or more trophic factors are selected from the group consisting of vascular endothelial growth factor, hepatocyte growth factor, bone morphogenetic protein 4, Dkk-1, fibroblast growth factor-7, heparin-binding epidermal growth factor-like growth factor, interleukin-6, interleukin-8, monocyte chemoattractant protein-1, matrix metalloproteinase-1, platelet-derived growth factor AA and transforming growth factor alpha.

16. A method for preventing death of neural cells in a host by provision of one or more trophic factors, wherein the method comprises transplanting bone marrow-derived neural regenerating cells at or near, a site of neural degeneration in the host, wherein the neural regenerating cells are obtained by a process comprising the steps of:
   (a) providing a culture of marrow adherent stromal cells;
   (b) contacting the cell culture of step (a) with a polynucleotide comprising sequences encoding a Notch intracellular domain (NICD), wherein the NICD consists of amino acids 1703-2504 of the Notch-1 protein;
   (c) selecting cells that comprise the polynucleotide of step (b); and
   (d) further culturing the selected cells of step (c) in the absence of selection;
   and further wherein the neural regenerating cells provide trophic factors that prevent death of the neural cells in the host.

17. The method of claim 16, wherein said cell death is by apoptosis.

18. The method of claim 16, wherein the site of neural degeneration is in the central nervous system.

19. The method of claim 18, wherein the site of neural degeneration is caused by Parkinson's Disease.

20. The method of claim 16, wherein the site of neural degeneration is in the peripheral nervous system.

21. The method of claim 16, wherein the one or more trophic factors are selected from the group consisting of vascular endothelial growth factor, hepatocyte growth factor, bone morphogenetic protein 4, Dkk-1, fibroblast growth factor-7, heparin-binding epidermal growth factor-like growth factor, interleukin-6, interleukin-8, monocyte chemoattractant protein-1, matrix metalloproteinase-1, platelet-derived growth factor AA and transforming growth factor alpha.

* * * * *